United States Patent
Chien et al.

(10) Patent No.: US 6,630,298 B2
(45) Date of Patent: *Oct. 7, 2003

(54) HCV ANTIGEN/ANTIBODY COMBINATION ASSAY

(75) Inventors: David Y. Chien, Alamo, CA (US); Phillip Arcangel, Oakland, CA (US); Laura Tandeske, San Leandro, CA (US); Carlos George-Nascimento, Walnut Creek, CA (US); Doris Coit, Petaluma, CA (US); Angelica Medina-Selby, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/881,239

(22) Filed: Jun. 14, 2001

(65) Prior Publication Data

US 2002/0192639 A1 Dec. 19, 2002

Related U.S. Application Data

(60) Provisional application No. 60/212,082, filed on Jun. 15, 2000, provisional application No. 60/280,867, filed on Apr. 2, 2001, and provisional application No. 60/280,811, filed on Apr. 2, 2001.

(51) Int. Cl.[7] .................................................. C12Q 1/70
(52) U.S. Cl. .............................. 435/5; 436/518; 435/23
(58) Field of Search .............................. 435/5, 518, 23; 436/518

(56) References Cited

U.S. PATENT DOCUMENTS

| | | | |
|---|---|---|---|
| 5,350,671 | A | 9/1994 | Houghton et al. |
| 5,712,087 | A | 1/1998 | Houghton et al. |
| 5,843,752 | A | 12/1998 | Dasmahapatra et al. |
| 5,871,904 | A | 2/1999 | Kashiwakuma et al. |
| 5,990,276 | A | 11/1999 | Zhang et al. |
| 6,171,782 | B1 | 1/2001 | Houghton et al. |

FOREIGN PATENT DOCUMENTS

| | | |
|---|---|---|
| EP | 0 318 216 B2 | 5/1989 |
| EP | 0 388 231 | 9/1990 |
| EP | 0388232 A1 | 9/1990 |
| EP | 0 450 931 | 10/1991 |
| EP | 0 472 207 A2 * | 2/1992 |
| WO | WO 93/00365 | 1/1993 |
| WO | WO 97/44469 | 11/1993 |
| WO | WO 94/01778 | 1/1994 |

OTHER PUBLICATIONS

Cruse et al., Illustrated Dictionary of Immunology, CRC Press, Boca Raton FL, 1995, p. 76.*
Pereboeva et al., Hepatitis C Epitopes From Phage-Displayed cDNA Libraries and Improved Diagnosis With a Chimeric Antigen. Journal of Medical Virology 60:144–151, 2000.*
Beld et al., "Evaluation of Automated RNA–Extraction Technology and a Qualitative HCV Assay for Sensitivity and Detection of HCV RNA in Pool–Screening Systems," Transfusion 40:575–579 (2000).
Chien et al., "Diagnosis of Hepatitis C virus (HCV) Infection Using an Immunodominant Chimeric Polyprotein to Capture Circulating Antibodies: Revaluation of the Role of HCV in Liver Disease," Proc. Natl. Acad. Sci. U.S.A. 89:10011–10015 (1992).
Chien et al., "Use of Recombinant HCV Antigen in the Serodiagnosis of Hepatitis C virus Infection: significant Improvement in HCV Antibody Detection as Compared With the First Generation HCV C100–3 ELISA and the Synthetic Peptide EIA Tests," Journal of Gastroenterology and Hepatology 8:S33–39 (1993).
Choo et al., "Isolation of a cDNA Clone Derived from a Blood–Borne Non–A, Non–B Viral Hepatitis Genome," Science 244:359–362 (1989).
Choo et al., "Hepatitis C Virus: The Major Causative Agent of Viral Non–A, Non–B Hepatitis," British Medical Bulletin 46:423–441 (1990).
Ebeling et al., "Recombinant Immunoblot Assay for Hepatitis C Virus Antibody as Predictor of Infectivity," Lancet 335:982–983 (1990).
Houghton et al., "Molecular Biology of the Hepatitis C Viruses: Implications for Diagnosis, Development and Control of Viral Disease," Hepatology 14:381–388 (1991).
Kotwal et al., "Detection of Acute Hepatitis C Virus Infection by ELISA Using a Synthetic Peptide Comprising a Structural Epitope," Proc. Natl. Acad. Sci. U.S.A. 89: 4486–4489 (1992).
Kuo et al., "An Assay for Circulating Antibodies to a Major Etiologic Virus of Human Non–A, Non B Hepatitis," Science 244:362–364 (1989).
van der Poel et al., "Infectivity of Blood Seropositive for Hepatitis C Virus Antibodies," Lancet 335 :558–560 (1990).
van der Poel et al., "Confirmation of Hepatitis C Virus Infection by New Four–Antigen Recombinant Immunoblot Assay," Lancet 337:317–319 (1991).
Yao et al., "Molecular Views of Viral Polyprotein Processing Revealed by the Crystal Structure of the Hepatitis C Virus Bifunctional Protease–Helicase," Structure 7(11):1353–1363 (1999).
Chen et al. (1998) "Human and murine antibody recognition is focused on the ATPase/helicase domain, but not the protease domain to the hepatitis C virus non–structural 3 protein," Hepatology 28:219–224.

* cited by examiner

Primary Examiner—Donna C. Wortman
(74) Attorney, Agent, or Firm—Roberta L. Robins; Alisa A. Harbin; Robert P. Blackburn

(57) ABSTRACT

An HCV core antigen and NS3/4a antibody combination assay that can detect both HCV antigens and antibodies present in a sample using a single solid matrix, is provided, as well as immunoassay solid supports for use in the assay.

43 Claims, 16 Drawing Sheets

```
MSPIDPMGHHHHHHGRRRASVAAGILVPRGSPGLDGICSIEEFAPITAYAQQTRGLLGCIITSLTGRDKNQVE      73
GEVQIVSTAAQTFLATCINGVCWTVYHGAGTRTIASPKGPVIQMYTNVDQDLVGWPASQGTRSLTPCTCGSSD     146
LYLVTRHADVIPVRRGDSRGSLLSPRPISYLKGSAGGPLLCPAGHAVGIFRAAVCTRGVAKAVDFIPVENLE     219
TTMRSPVFTDNSSPPVPQSFQVAHLHAPTGSGKSTKVPAAYAAQGYKVLVLNPSVAATLGFGAYMSKAHGID     292
PNIRTGVRTITTGSPITYSTYGKFLADGGCSGGAYDIICDECHSTDATSILGIGTVLDQAETAGARLVVLAT     365
ATPPGSVTVPHPNIEEVALSTTGEIPFYGKAIPLEVIKGGRHLIFCHSKKKCDELAAKLVALGINAVAYYRGL    438
DVSVIPPIGDVVVATDALMTGYTGDFDSVIDCNTCVTQTVDFSLDPTFTIETITLPQDAVSRTQRRGRTGRG    511
KPGIYRFVAPGERPSGMFDSSVLCECYDAGCAWYELTPAETTVRLRAYMNTPGLPVCQDHLEFWECVFTGLTH   584
IDAHFLSQTKQSGENLPYLVAYQATVCARAQAPPPSWDQMWKCLIRLKPTLHGPTPLLYRLGAVQNEITLTHP   657
VTKYIMTCMSADLEVVTSTWVLVGGVLAALAAYCLSTGCVVVGRVVLSGKPAIIPDREVLYREFDEMEEC      728
```

FIG. 3

```
                              1                                        10
                              M   A   P   I   T   A   Y   A   Q   Q
                             ATG GCG CCC ATC ACG GCG TAC GCC CAG CAG

20
     T   R   G   L   L   G   C   I   I   T   S   L   T   G   R
    ACA AGG GGC CTC CTA GGG TGC ATA ATC ACC AGC CTA ACT GGC CGG 30                                          40
     D   K   N   Q   V   E   G   E   V   Q   I   V   S   T   A
    GAC AAA AAC CAA GTG GAG GGT GAG GTC CAG ATT GTG TCA ACT GCT

50
     A   Q   T   F   L   A   T   C   I   N   G   V   C   W   T
    GCC CAA ACC TTC CTG GCA ACG TGC ATC AAT GGG GTG TGC TGG ACT 60                                     70
     V   Y   H   G   A   G   T   R   T   I   A   S   P   K   G
    GTC TAC CAC GGG GCC GGA ACG AGG ACC ATC GCG TCA CCC AAG GGT

80
     P   V   I   Q   M   Y   T   N   V   D   Q   D   L   V   G
    CCT GTC ATC CAG ATG TAT ACC AAT GTA GAC CAA GAC CTT GTG GGC 90                                         100
     W   P   A   P   Q   G   S   R   S   L   T   P   C   T   C
    TGG CCC GCT CCG CAA GGT AGC CGA TCA TTG ACA CCC TGC ACT TGC

110
     G   S   S   D   L   Y   L   V   T   R   H   A   D   V   I
    GGC TCC TCG GAC CTT TAC CTG GTC ACG AGG CAC GCC GAT GTC ATT 120                                    130
     P   V   R   R   R   G   D   S   R   G   S   L   L   S   P
    CCC GTG CGC CGG CGG GGT GAT AGC AGG GGC AGC CTG CTG TCG CCC

140
     R   P   I   S   Y   L   K   G   S   S   G   G   P   L   L
    CGG CCC ATT TCC TAC TTG AAA GGC TCC TCG GGG GGT CCG CTG TTG 150                                    160
     C   P   A   G   H   A   V   G   I   F   R   A   A   V   C
    TGC CCC GCG GGG CAC GCC GTG GGC ATA TTT AGG GCC GCG GTG TGC

170
     T   R   G   V   A   K   A   V   D   F   I   P   V   E   N
    ACC CGT GGA GTG GCT AAG GCG GTG GAC TTT ATC CCT GTG GAG AAC 180                                    190
     L   E   T   T   M   R   S   P   V   F   T   D   N   S   S
    CTA GAG ACA ACC ATG AGG TCC CCG GTG TTC ACG GAT AAC TCC TCT
```

FIG. 4A

```
         P   P   V   V   P   Q   S   F   Q   V   A   H   L   H   A
        CCA CCA GTA GTG CCC CAG AGC TTC CAG GTG GCT CAC CTC CAT GCT 210                                     220
         P   T   G   S   G   K   S   T   K   V   P   A   A   Y   A
        CCC ACA GGC AGC GGC AAA AGC ACC AAG GTC CCG GCT GCA TAT GCA

230
         A   Q   G   Y   K   V   L   V   L   N   P   S   V   A   A
        GCT CAG GGC TAT AAG GTG CTA GTA CTC AAC CCC TCT GTT GCT GCA 240                                     250
         T   L   G   F   G   A   Y   M   S   K   A   H   G   I   D
        ACA CTG GGC TTT GGT GCT TAC ATG TCC AAG GCT CAT GGG ATC GAT

260
         P   N   I   R   T   G   V   R   T   I   T   T   G   S   P
        CCT AAC ATC AGG ACC GGG GTG AGA ACA ATT ACC ACT GGC AGC CCC 270                                     280
         I   T   Y   S   T   Y   G   K   F   L   A   D   G   G   C
        ATC ACG TAC TCC ACC TAC GGC AAG TTC CTT GCC GAC GGC GGG TGC

290
         S   G   G   A   Y   D   I   I   I   C   D   E   C   H   S
        TCG GGG GGC GCT TAT GAC ATA ATA ATT TGT GAC GAG TGC CAC TCC 300                                     310
         T   D   A   T   S   I   L   G   I   G   T   V   L   D   Q
        ACG GAT GCC ACA TCC ATC TTG GGC ATT GGC ACT GTC CTT GAC CAA

320
         A   E   T   A   G   A   R   L   V   V   L   A   T   A   T
        GCA GAG ACT GCG GGG GCG AGA CTG GTT GTG CTC GCC ACC GCC ACC 330                                     340
         P   P   G   S   V   T   V   P   H   P   N   I   E   E   V
        CCT CCG GGC TCC GTC ACT GTG CCC CAT CCC AAC ATC GAG GAG GTT

350
         A   L   S   T   T   G   E   I   P   F   Y   G   K   A   I
        GCT CTG TCC ACC ACC GGA GAG ATC CCT TTT TAC GGC AAG GCT ATC 360                                     370
         P   L   E   V   I   K   G   G   R   H   L   I   F   C   H
        CCC CTC GAA GTA ATC AAG GGG GGG AGA CAT CTC ATC TTC TGT CAT

380
         S   K   K   K   C   D   E   L   A   A   K   L   V   A   L
        TCA AAG AAG AAG TGC GAC GAA CTC GCC GCA AAG CTG GTC GCA TTG
```

FIG. 4B

```
        390                                          400
 G   I   N   A   V   A   Y   Y   R   G   L   D   V   S   V
GGC ATC AAT GCC GTG GCC TAC TAC CGC GGT CTT GAC GTG TCC GTC

410
 I   P   P   I   G   D   V   V   V   A   T   D   A   L
ATC CCG CCC ATC GGC GAT GTT GTC GTC GTG GCA ACC GAT GCC CTC 420                                 430
 M   T   G   Y   T   G   D   F   D   S   V   I   D   C   N
ATG ACC GGC TAT ACG GGC GAC TTC GAC TCG GTG ATA GAC TGC AAT

440
 T   C   V   T   Q   T   V   D   F   S   L   D   P   T   F
ACG TGT GTC ACC CAG ACA GTC GAT TTC AGC CTT GAC CCT ACC TTC 450                                 460
 T   I   E   T   I   T   L   P   Q   D   A   V   S   R   T
ACC ATT GAG ACA ATC ACG CTC CCC CAA GAT GCT GTC TCC CGC ACT

470
 Q   R   R   G   R   T   G   R   G   K   P   G   I   Y   R
CAA CGT CGG GGC AGG ACT GGC AGG GGG AAG CCA GGC ATC TAC AGA 480                                 490
 F   V   A   P   G   E   R   P   S   G   M   F   D   S   S
TTT GTG GCA CCG GGG GAG CGC CCC TCC GGC ATG TTC GAC TCG TCC

500
 V   L   C   E   C   Y   D   A   G   C   A   W   Y   E   L
GTC CTC TGT GAG TGC TAT GAC GCA GGC TGT GCT TGG TAT GAG CTC 510                                 520
 T   P   A   E   T   T   V   R   L   R   A   Y   M   N   T
ACG CCC GCC GAG ACT ACA GTT AGG CTA CGA GCG TAC ATG AAC ACC

530
 P   G   L   P   V   C   Q   D   H   L   E   F   W   E   G
CCG GGG CTT CCC GTG TGC CAG GAC CAT CTT GAA TTT TGG GAG GGC 540                                 550
 V   F   T   G   L   T   H   I   D   A   H   F   L   S   Q
GTC TTT ACA GGC CTC ACT CAT ATA GAT GCC CAC TTT CTA TCC CAG

560
 T   K   Q   S   G   E   N   L   P   Y   L   V   A   Y   Q
ACA AAG CAG AGT GGG GAG AAC CTT CCT TAC CTG GTA GCG TAC CAA 570                                 580
 A   T   V   C   A   R   A   Q   A   P   P   P   S   W   D
GCC ACC GTG TGC GCT AGG GCT CAA GCC CCT CCC CCA TCG TGG GAC
```

FIG. 4C

```
                                            590
Q    M    W    K    C    L    I    R    L    K    P    T    L    H    G
CAG  ATG  TGG  AAG  TGT  TTG  ATT  CGC  CTC  AAG  CCC  ACC  CTC  CAT  GGG 600                                                 610
P    T    P    L    L    Y    R    L    G    A    V    Q    N    E    I
CCA  ACA  CCC  CTG  CTA  TAC  AGA  CTG  GGC  GCT  GTT  CAG  AAT  GAA  ATC

620
T    L    T    H    P    V    T    K    Y    I    M    T    C    M    S
ACC  CTG  ACG  CAC  CCA  GTC  ACC  AAA  TAC  ATC  ATG  ACA  TGC  ATG  TCG 630                                                 640
A    D    L    E    V    V    T    S    T    W    V    L    V    G    G
GCC  GAC  CTG  GAG  GTC  GTC  ACG  AGC  ACC  TGG  GTG  CTC  GTT  GGC  GGC

650
V    L    A    A    L    A    A    Y    C    L    S    T    G    C    V
GTC  CTG  GCT  GCT  TTG  GCC  GCG  TAT  TGC  CTG  TCA  ACA  GGC  TGC  GTG 660                                                 670
V    I    V    G    R    V    V    L    S    G    K    P    A    I    I
GTC  ATA  GTG  GGC  AGG  GTC  GTC  TTG  TCC  GGG  AAG  CCG  GCA  ATC  ATA

680
P    D    R    E    V    L    Y    R    E    F    D    E    M    E    E
CCT  GAC  AGG  GAA  GTC  CTC  TAC  CGA  GAG  TTC  GAT  GAG  ATG  GAA  GAG

686
C
TGC
```

FIG. 4D

MEFA 12 Antigen Construct

▨ SOD    ▨ C33c short    ☐ 5-1-1: 1+3+2    ⊞ Core 1+2

▨ E1

☐ E2 HVR1a    ▨ C100-1 C-terminal

☐ E2 HVR 1+2 concensus    ⊠ NS5 major 1a

FIG. 6

```
  1                                      10
  M   A   T   K   A   V   C   V   L   K   G   D   G   P   V
 ATG GCT ACA AAG GCT GTT TGT GTT TTG AAG GGT GAC GGC CCA GTT    45

20                                      30
  Q   G   I   I   N   F   E   Q   K   E   S   N   G   P   V
 CAA GGT ATT ATT AAC TTC GAG CAG AAG GAA AGT AAT GGA CCA GTG    90

40
  K   V   W   G   S   I   K   G   L   T   E   G   L   H   G
 AAG GTG TGG GGA AGC ATT AAA GGA CTG ACT GAA GGC CTG CAT GGA   135

50                                      60
  F   H   V   H   E   F   G   D   N   T   A   G   C   T   S
 TTC CAT GTT CAT GAG TTT GGA GAT AAT ACA GCA GGC TGT ACC AGT   180

70
  A   G   P   H   F   N   P   L   S   T   R   G   C   N   C
 GCA GGT CCT CAC TTT AAT CCT CTA TCC ACG CGT GGT TGC AAT TGC   225

80                                      90
  S   I   Y   P   G   H   I   T   G   H   R   M   A   W   K
 TCT ATC TAT CCC GGC CAT ATA ACG GGT CAC CGC ATG GCA TGG AAG   270

100
  L   G   S   A   A   R   T   T   S   G   F   V   S   L   F
 CTT GGT TCC GCC GCC AGA ACT ACC TCG GGC TTT GTC TCC TTG TTC   315

110                                     120
  A   P   G   A   K   Q   N   E   T   H   V   T   G   G   A
 GCC CCA GGT GCC AAA CAA AAC GAA ACT CAC GTC ACG GGA GGC GCA   360

130
  A   A   R   T   T   S   G   L   T   S   L   F   S   P   G
 GCC GCC CGA ACT ACG TCT GGG TTG ACC TCT TTG TTC TCC CCA GGT   405
```

FIG. 7A

```
                                140                                            150
       A    S    Q    N    I    Q    L    I    T    S    T    D    N    S    S
      GCC  AGC  CAA  AAC  ATT  CAA  TTG  ATT  ACT  AGT  ACG  GAT  AAC  TCC  TCT    450

160
       P    P    V    V    P    Q    S    F    Q    V    A    H    L    H    A
      CCA  CCA  GTA  GTG  CCC  CAG  AGC  TTC  CAG  GTG  GCT  CAC  CTC  CAT  GCT    495

170                                                 180
       P    T    G    S    G    K    S    T    K    V    P    A    A    Y    A
      CCC  ACA  GGC  AGC  GGC  AAA  AGC  ACC  AAG  GTC  CCG  GCT  GCA  TAT  GCA    540

190
       A    Q    G    Y    K    V    L    V    L    N    P    S    V    A    A
      GCT  CAG  GGC  TAT  AAG  GTG  CTA  GTA  CTC  AAC  CCC  TCT  GTT  GCT  GCA    585

200                                                 210
       T    L    G    F    G    A    Y    M    S    K    A    H    G    I    D
      ACA  CTG  GGC  TTT  GGT  GCT  TAC  ATG  TCC  AAG  GCT  CAT  GGG  ATC  GAT    630

220
       P    N    I    R    T    G    V    R    T    I    T    T    G    S    P
      CCT  AAC  ATC  AGG  ACC  GGG  GTG  AGA  ACA  ATT  ACC  ACT  GGC  AGC  CCC    675

230                                            240
       I    T    Y    S    T    Y    G    K    F    L    A    D    G    G    C
      ATC  ACG  TAC  TCC  ACC  TAC  GGC  AAG  TTC  CTT  GCC  GAC  GGC  GGG  TGC    720

250
       S    G    G    A    Y    D    I    I    I    C    D    E    C    H    S
      TCG  GGG  GGC  GCT  TAT  GAC  ATA  ATA  ATT  TGT  GAC  GAG  TGC  CAC  TCC    765

260                                            270
       T    D    A    T    S    I    L    G    I    G    T    V    L    D    Q
      ACG  GAT  GCC  ACA  TCC  ATC  TTG  GGC  ATC  GGC  ACT  GTC  CTT  GAC  CAA    810

280
       A    E    T    A    G    A    R    L    V    V    L    A    T    A    T
      GCA  GAG  ACT  GCG  GGG  GCG  AGA  CTG  GTT  GTG  CTC  GCC  ACC  GCC  ACC    855

290                                            300
       P    P    G    S    V    T    V    P    H    P    N    I    E    E    V
      CCT  CCG  GGC  TCC  GTC  ACT  GTG  CCC  CAT  CCC  AAC  ATC  GAG  GAG  GTT    900
```

FIG. 7B

```
       A   L   S   T   T   G   E   I   P   F   Y   G   K   A   I
                                   310
      GCT CTG TCC ACC ACC GGA GAG ATC CCT TTT TAC GGC AAG GCT ATC    945

P   L   E   V   I   K   G   G   R   H   L   I   F   C   H
                   320                                   330
      CCC CTC GAA GTA ATC AAG GGG GGG AGA CAT CTC ATC TTC TGT CAT    990

S   K   K   K   C   D   E   L   A   A   K   L   V   A   L
                                   340
      TCA AAG AAG AAG TGC GAC GAA CTC GCC GCA AAG CTG GTC GCA TTG   1035

G   I   N   A   V   A   Y   Y   R   G   L   D   V   S   V
                   350                                   360
      GGC ATC AAT GCC GTG GCC TAC TAC CGC GGT CTT GAC GTG TCC GTC   1080

I   P   T   S   G   D   V   V   V   V   A   T   D   A   L
                                   370
      ATC CCG ACC AGC GGC GAT GTT GTC GTC GTG GCA ACC GAT GCC CTC   1125

M   T   G   Y   T   G   D   F   D   S   V   I   D   C   N
                   380                                   390
      ATG ACC GGC TAT ACC GGC GAC TTC GAC TCG GTG ATA GAC TGC AAT   1170

T   C   A   C   S   G   K   P   A   I   I   P   D   R   E
                                   400
      ACG TGT GCA TGC TCC GGG AAG CCG GCA ATC ATA CCT GAC AGG GAA   1215

V   L   Y   R   E   F   D   E   M   E   E   C   S   Q   H
                   410                                   420
      GTC CTC TAC CGA GAG TTC GAT GAG ATG GAA GAG TGC TCT CAG CAC   1260

L   P   Y   I   E   Q   G   M   M   L   A   E   Q   F   K
                                   430
      TTA CCG TAC ATC GAG CAA GGG ATG ATG CTC GCC GAG CAG TTC AAG   1305

Q   K   A   L   G   L   S   R   G   G   K   P   A   I   V
                   440                                   450
      CAG AAG GCC CTC GGC CTC TCG CGA GGG GGC AAG CCG GCA ATC GTT   1350

P   D   K   E   V   L   Y   Q   Q   Y   D   E   M   E   E
                                   460
      CCA GAC AAA GAG GTG TTG TAT CAA CAA TAC GAT GAG ATG GAA GAG   1395
```

FIG. 7C

```
                    470                                               480
     C    S    Q    A    A    P    Y    I    E    Q    A    Q    V    I    A
    TGC  TCA  CAA  GCT  GCC  CCA  TAT  ATC  GAA  CAA  GCT  CAG  GTA  ATA  GCT    1440

490
     H    Q    F    K    E    K    V    L    G    L    I    D    N    D    Q
    CAC  CAG  TTC  AAG  GAA  AAA  GTC  CTT  GGA  TTG  ATC  GAT  AAT  GAT  CAA    1485

500                                          510
     V    V    V    T    P    D    K    E    I    L    Y    E    A    F    D
    GTG  GTT  GTG  ACT  CCT  GAC  AAA  GAA  ATC  TTA  TAT  GAG  GCC  TTT  GAT    1530

520
     E    M    E    E    C    A    S    K    A    A    L    I    E    E    G
    GAG  ATG  GAA  GAA  TGC  GCC  TCC  AAA  GCC  GCC  CTC  ATT  GAG  GAA  GGG    1575

530                                               540
     Q    R    M    A    E    M    L    K    S    K    I    Q    G    L    L
    CAG  CGG  ATG  GCG  GAG  ATG  CTC  AAG  TCT  AAG  ATA  CAA  GGC  CTC  CTC    1625

550
     G    I    L    R    R    H    V    G    P    G    E    G    A    V    Q
    GGG  ATA  CTG  CGC  CGG  CAC  GTT  GGT  CCT  GGC  GAG  GGG  GCA  GTG  CAG    1670

560                                          570
     W    M    N    R    L    I    A    F    A    S    R    G    N    H    V
    TGG  ATG  AAC  CGG  CTG  ATA  GCC  TTC  GCC  TCC  AGA  GGG  AAC  CAT  GTT    1715

580
     S    P    T    H    Y    V    P    S    R    S    R    R    F    A    Q
    TCC  CCC  ACG  CAC  TAC  GTT  CCG  TCT  AGA  TCC  CGG  AGA  TTC  GCC  CAG    1760

590                                               600
     A    L    P    V    W    A    R    P    D    Y    N    P    P    L    V
    GCC  CTG  CCC  GTT  TGG  GCG  CGG  CCG  GAC  TAT  AAC  CCC  CCG  CTA  GTG    1805

610
     E    T    W    K    K    P    D    Y    E    P    P    V    V    H    G
    GAG  ACG  TGG  AAA  AAG  CCC  GAC  TAC  GAA  CCA  CCT  GTG  GTC  CAC  GGC    1850

620                                          630
     R    S    S    R    R    F    A    Q    A    L    P    V    W    A    R
    AGA  TCT  TCT  CGG  AGA  TTC  GCC  CAG  GCC  CTG  CCC  GTT  TGG  GCG  CGG    1895
```

FIG. 7D

```
          P   D   Y   N   P   P   L   V   E   T   W   K   K   P   D
                                      640
         CCG GAC TAT AAC CCC CCG CTA GTG GAG ACG TGG AAA AAG CCC GAC   1940

Y   E   P   P   V   V   H   G   R   K   T   K   R   N   T
                      650                                 660
         TAC GAA CCA CCT GTG GTC CAT GGC AGA AAG ACC AAA CGT AAC ACC   1985

N   R   R   P   Q   D   V   K   F   P   G   G   G   Q   I
                                          670
         AAC CGG CGG CCG CAG GAC GTC AAG TTC CCG GGT GGC GGT CAG ATC   2030

V   G   G   V   Y   L   L   P   R   R   G   P   R   L   G
                      680                                 690
         GTT GGT GGA GTT TAC TTG TTG CCG CGC AGG GGC CCT AGA TTG GGT   2075

V   L   A   T   R   K   T   S   P   I   P   K   A   R   R
                                      700
         GTG CTC GCG ACG AGA AAG ACT TCC CCT ATC CCC AAG GCT CGT CGG   2120

P   E   G   R   T   W   A   Q   P   G   Y   P   W   P   L
                      710                                 720
         CCC GAG GGC AGG ACC TGG GCT CAG CCC GGT TAC CCT TGG CCC CTC   2165

Y   G   N   K   D   R   R   S   T   G   K   S   W   G   K
                                      730
         TAT GGC AAT AAG GAC AGA CGG TCT ACA GGT AAG TCC TGG GGT AAG   2210

P   G   Y   P   W   P   R   K   T   K   R   N   T   N   R
                      740                                 750
         CCA GGG TAC CCT TGG CCA AGA AAG ACC AAA CGT AAC ACC AAC CGG   2255

R   P   Q   D   V   K   F   P   G   G   G   Q   I   V   G
                                      760
         CGG CCG CAG GAC GTC AAG TTC CCG GGT GGC GGT CAG ATC GTT GGT   2300

G   V   Y   L   L   P   R   R   G   P   R   L   G   V   L
                      770                                 780
         GGA GTT TAC TTG TTG CCG CGC AGG GGC CCT AGA TTG GGT GTG CTC   2345

A   T   R   K   T   S   P   I   P   K   A   R   R   P   E
                                      790
         GCG ACG AGA AAG ACT TCC CCT ATC CCC AAG GCT CGT CGG CCC GAG   2390
```

FIG. 7E

```
              800                                     810-
   G   R   T   W   A   Q   P   G   Y   P   W   P   L   Y   G
  GGC AGG ACC TGG GCT CAG CCC GGT TAC CCT TGG CCC CTC TAT GGC   2435

820
   N   K   D   R   R   S   T   G   K   S   W   G   K   P   G
  AAT AAG GAC AGA CGG TCT ACA GGT AAG TCC TGG GGT AAG CCA GGG   2480

829
   Y   P   W   P   OC
  TAC CCT TGG CCC TAA TGAGTCGAC
```

FIG. 7F

SEQUENCE LISTING

<160> NUMBER OF SEQ ID NOS: 8

<210> SEQ ID NO 1
<211> LENGTH: 728
<212> TYPE: PRT
<213> ORGANISM: Artificial Sequence
<220> FEATURE:
<223> OTHER INFORMATION: Description of Artificial Sequence:
      representative NS3/4a conformational antigen

<400> SEQUENCE: 1

Met Ser Pro Ile Asp Pro Met Gly His His His His His Gly Arg
 1               5                  10                  15

Arg Arg Ala Ser Val Ala Ala Gly Ile Leu Val Pro Arg Gly Ser Pro
                20                  25                  30

Gly Leu Asp Gly Ile Cys Ser Ile Glu Glu Phe Ala Pro Ile Thr Ala
            35                  40                  45

Tyr Ala Gln Gln Thr Arg Gly Leu Leu Gly Cys Ile Ile Thr Ser Leu
     50                  55                  60

Thr Gly Arg Asp Lys Asn Gln Val Glu Gly Glu Val Gln Ile Val Ser
 65                  70                  75                  80

Thr Ala Ala Gln Thr Phe Leu Ala Thr Cys Ile Asn Gly Val Cys Trp
                85                  90                  95

Thr Val Tyr His Gly Ala Gly Thr Arg Thr Ile Ala Ser Pro Lys Gly
            100                 105                 110

Pro Val Ile Gln Met Tyr Thr Asn Val Asp Gln Asp Leu Val Gly Trp
        115                 120                 125

Pro Ala Ser Gln Gly Thr Arg Ser Leu Thr Pro Cys Thr Cys Gly Ser
130                 135                 140

Ser Asp Leu Tyr Leu Val Thr Arg His Ala Asp Val Ile Pro Val Arg
145                 150                 155                 160

Arg Arg Gly Asp Ser Arg Gly Ser Leu Leu Ser Pro Arg Pro Ile Ser
                165                 170                 175

Tyr Leu Lys Gly Ser Ala Gly Gly Pro Leu Leu Cys Pro Ala Gly His
            180                 185                 190

Ala Val Gly Ile Phe Arg Ala Ala Val Cys Thr Arg Gly Val Ala Lys
        195                 200                 205

Ala Val Asp Phe Ile Pro Val Glu Asn Leu Glu Thr Thr Met Arg Ser
    210                 215                 220

Pro Val Phe Thr Asp Asn Ser Ser Pro Pro Val Val Pro Gln Ser Phe
225                 230                 235                 240

Gln Val Ala His Leu His Ala Pro Thr Gly Ser Gly Lys Ser Thr Lys
                245                 250                 255

Val Pro Ala Ala Tyr Ala Ala Gln Gly Tyr Lys Val Leu Val Leu Asn
            260                 265                 270

Pro Ser Val Ala Ala Thr Leu Gly Phe Gly Ala Tyr Met Ser Lys Ala
        275                 280                 285

His Gly Ile Asp Pro Asn Ile Arg Thr Gly Val Arg Thr Ile Thr Thr
    290                 295                 300

Gly Ser Pro Ile Thr Tyr Ser Thr Tyr Gly Lys Phe Leu Ala Asp Gly
305                 310                 315                 320

Gly Cys Ser Gly Gly Ala Tyr Asp Ile Ile Cys Asp Glu Cys His
                325                 330                 335

Ser Thr Asp Ala Thr Ser Ile Leu Gly Ile Gly Thr Val Leu Asp Gln

```
                    340                 345                 350
Ala Glu Thr Ala Gly Ala Arg Leu Val Val Leu Ala Thr Ala Thr Pro
                355                 360                 365

Pro Gly Ser Val Thr Val Pro His Pro Asn Ile Glu Glu Val Ala Leu
            370                 375                 380

Ser Thr Thr Gly Glu Ile Pro Phe Tyr Gly Lys Ala Ile Pro Leu Glu
385                 390                 395                 400

Val Ile Lys Gly Gly Arg His Leu Ile Phe Cys His Ser Lys Lys Lys
                405                 410                 415

Cys Asp Glu Leu Ala Ala Lys Leu Val Ala Leu Gly Ile Asn Ala Val
            420                 425                 430

Ala Tyr Tyr Arg Gly Leu Asp Val Ser Val Ile Pro Pro Ile Gly Asp
                435                 440                 445

Val Val Val Ala Thr Asp Ala Leu Met Thr Gly Tyr Thr Gly Asp
            450                 455                 460

Phe Asp Ser Val Ile Asp Cys Asn Thr Cys Val Thr Gln Thr Val Asp
465                 470                 475                 480

Phe Ser Leu Asp Pro Thr Phe Thr Ile Glu Thr Ile Thr Leu Pro Gln
                485                 490                 495

Asp Ala Val Ser Arg Thr Gln Arg Arg Gly Arg Thr Gly Arg Gly Lys
            500                 505                 510

Pro Gly Ile Tyr Arg Phe Val Ala Pro Gly Glu Arg Pro Ser Gly Met
                515                 520                 525

Phe Asp Ser Ser Val Leu Cys Glu Cys Tyr Asp Ala Gly Cys Ala Trp
            530                 535                 540

Tyr Glu Leu Thr Pro Ala Glu Thr Thr Val Arg Leu Arg Ala Tyr Met
545                 550                 555                 560

Asn Thr Pro Gly Leu Pro Val Cys Gln Asp His Leu Glu Phe Trp Glu
                565                 570                 575

Gly Val Phe Thr Gly Leu Thr His Ile Asp Ala His Phe Leu Ser Gln
            580                 585                 590

Thr Lys Gln Ser Gly Glu Asn Leu Pro Tyr Leu Val Ala Tyr Gln Ala
                595                 600                 605

Thr Val Cys Ala Arg Ala Gln Ala Pro Pro Ser Trp Asp Gln Met
            610                 615                 620

Trp Lys Cys Leu Ile Arg Leu Lys Pro Thr Leu His Gly Pro Thr Pro
625                 630                 635                 640

Leu Leu Tyr Arg Leu Gly Ala Val Gln Asn Glu Ile Thr Leu Thr His
                645                 650                 655

Pro Val Thr Lys Tyr Ile Met Thr Cys Met Ser Ala Asp Leu Glu Val
                660                 665                 670

Val Thr Ser Thr Trp Val Leu Val Gly Gly Val Leu Ala Ala Leu Ala
            675                 680                 685

Ala Tyr Cys Leu Ser Thr Gly Cys Val Val Ile Val Gly Arg Val Val
            690                 695                 700

Leu Ser Gly Lys Pro Ala Ile Ile Pro Asp Arg Glu Val Leu Tyr Arg
705                 710                 715                 720

Glu Phe Asp Glu Met Glu Glu Cys
                725

<210> SEQ ID NO 2
<211> LENGTH: 2058
<212> TYPE: DNA
<213> ORGANISM: Artificial Sequence
```

-continued

```
<220> FEATURE:
<223> OTHER INFORMATION: Description of Artificial Sequence:
      representative NS3/4a conformational antigen
<221> NAME/KEY: CDS
<222> LOCATION: (1)..(2058)

<400> SEQUENCE: 2 atg gcg ccc atc acg gcg tac gcc cag cag aca agg ggc ctc cta ggg        48
Met Ala Pro Ile Thr Ala Tyr Ala Gln Gln Thr Arg Gly Leu Leu Gly
 1               5                  10                  15 tgc ata atc acc agc cta act ggc cgg gac aaa aac caa gtg gag ggt        96
Cys Ile Ile Thr Ser Leu Thr Gly Arg Asp Lys Asn Gln Val Glu Gly
             20                  25                  30 gag gtc cag att gtg tca act gct gcc caa acc ttc ctg gca acg tgc       144
Glu Val Gln Ile Val Ser Thr Ala Ala Gln Thr Phe Leu Ala Thr Cys
         35                  40                  45 atc aat ggg gtg tgc tgg act gtc tac cac ggg gcc gga acg agg acc       192
Ile Asn Gly Val Cys Trp Thr Val Tyr His Gly Ala Gly Thr Arg Thr
     50                  55                  60 atc gcg tca ccc aag ggt cct gtc atc cag atg tat acc aat gta gac       240
Ile Ala Ser Pro Lys Gly Pro Val Ile Gln Met Tyr Thr Asn Val Asp
 65                  70                  75                  80 caa gac ctt gtg ggc tgg ccc gct ccg caa ggt agc cga tca ttg aca       288
Gln Asp Leu Val Gly Trp Pro Ala Pro Gln Gly Ser Arg Ser Leu Thr
                 85                  90                  95 ccc tgc act tgc ggc tcc tcg gac ctt tac ctg gtc acg agg cac gcc       336
Pro Cys Thr Cys Gly Ser Ser Asp Leu Tyr Leu Val Thr Arg His Ala
            100                 105                 110 gat gtc att ccc gtg cgc cgg cgg ggt gat agc agg ggc agc ctg ctg       384
Asp Val Ile Pro Val Arg Arg Arg Gly Asp Ser Arg Gly Ser Leu Leu
        115                 120                 125 tcg ccc cgg ccc att tcc tac ttg aaa ggc tcc tcg ggg ggt ccg ctg       432
Ser Pro Arg Pro Ile Ser Tyr Leu Lys Gly Ser Ser Gly Gly Pro Leu
    130                 135                 140 ttg tgc ccc gcg ggg cac gcc gtg ggc ata ttt agg gcc gcg gtg tgc       480
Leu Cys Pro Ala Gly His Ala Val Gly Ile Phe Arg Ala Ala Val Cys
145                 150                 155                 160 acc cgt gga gtg gct aag gcg gtg gac ttt atc cct gtg gag aac cta       528
Thr Arg Gly Val Ala Lys Ala Val Asp Phe Ile Pro Val Glu Asn Leu
                165                 170                 175 gag aca acc atg agg tcc ccg gtg ttc acg gat aac tcc tct cca cca       576
Glu Thr Thr Met Arg Ser Pro Val Phe Thr Asp Asn Ser Ser Pro Pro
            180                 185                 190 gta gtg ccc cag agc ttc cag gtg gct cac ctc cat gct ccc aca ggc       624
Val Val Pro Gln Ser Phe Gln Val Ala His Leu His Ala Pro Thr Gly
        195                 200                 205 agc ggc aaa agc acc aag gtc ccg gct gca tat gca gct cag ggc tat       672
Ser Gly Lys Ser Thr Lys Val Pro Ala Ala Tyr Ala Ala Gln Gly Tyr
    210                 215                 220 aag gtg cta gta ctc aac ccc tct gtt gct gca aca ctg ggc ttt ggt       720
Lys Val Leu Val Leu Asn Pro Ser Val Ala Ala Thr Leu Gly Phe Gly
225                 230                 235                 240 gct tac atg tcc aag gct cat ggg atc gat cct aac atc agg acc ggg       768
Ala Tyr Met Ser Lys Ala His Gly Ile Asp Pro Asn Ile Arg Thr Gly
                245                 250                 255 gtg aga aca att acc act ggc agc ccc atc acg tac tcc acc tac ggc       816
Val Arg Thr Ile Thr Thr Gly Ser Pro Ile Thr Tyr Ser Thr Tyr Gly
            260                 265                 270 aag ttc ctt gcc gac ggg ggg tgc tcg ggg ggc gct tat gac ata ata       864
Lys Phe Leu Ala Asp Gly Gly Cys Ser Gly Gly Ala Tyr Asp Ile Ile
        275                 280                 285
```

```
att tgt gac gag tgc cac tcc acg gat gcc aca tcc atc ttg ggc att          912
Ile Cys Asp Glu Cys His Ser Thr Asp Ala Thr Ser Ile Leu Gly Ile
    290                 295                 300 ggc act gtc ctt gac caa gca gag act gcg ggg gcg aga ctg gtt gtg          960
Gly Thr Val Leu Asp Gln Ala Glu Thr Ala Gly Ala Arg Leu Val Val
305                 310                 315                 320 ctc gcc acc gcc acc cct ccg ggc tcc gtc act gtg ccc cat ccc aac         1008
Leu Ala Thr Ala Thr Pro Pro Gly Ser Val Thr Val Pro His Pro Asn
                325                 330                 335 atc gag gag gtt gct ctg tcc acc acc gga gag atc cct ttt tac ggc         1056
Ile Glu Glu Val Ala Leu Ser Thr Thr Gly Glu Ile Pro Phe Tyr Gly
            340                 345                 350 aag gct atc ccc ctc gaa gta atc aag ggg ggg aga cat ctc atc ttc         1104
Lys Ala Ile Pro Leu Glu Val Ile Lys Gly Gly Arg His Leu Ile Phe
        355                 360                 365 tgt cat tca aag aag aag tgc gac gaa ctc gcc gca aag ctg gtc gca         1152
Cys His Ser Lys Lys Lys Cys Asp Glu Leu Ala Ala Lys Leu Val Ala
    370                 375                 380 ttg ggc atc aat gcc gtg gcc tac tac cgc ggt ctt gac gtg tcc gtc         1200
Leu Gly Ile Asn Ala Val Ala Tyr Tyr Arg Gly Leu Asp Val Ser Val
385                 390                 395                 400 atc ccg ccc atc ggc gat gtt gtc gtc gtg gca acc gat gcc ctc atg         1248
Ile Pro Pro Ile Gly Asp Val Val Val Val Ala Thr Asp Ala Leu Met
                405                 410                 415 acc ggc tat acc ggc gac ttc gac tcg gtg ata gac tgc aat acg tgt         1296
Thr Gly Tyr Thr Gly Asp Phe Asp Ser Val Ile Asp Cys Asn Thr Cys
            420                 425                 430 gtc acc cag aca gtc gat ttc agc ctt gac cct acc ttc acc att gag         1344
Val Thr Gln Thr Val Asp Phe Ser Leu Asp Pro Thr Phe Thr Ile Glu
        435                 440                 445 aca atc acg ctc ccc caa gat gct gtc tcc cgc act caa cgt cgg ggc         1392
Thr Ile Thr Leu Pro Gln Asp Ala Val Ser Arg Thr Gln Arg Arg Gly
    450                 455                 460 agg act ggc agg ggg aag cca ggc atc tac aga ttt gtg gca ccg ggg         1440
Arg Thr Gly Arg Gly Lys Pro Gly Ile Tyr Arg Phe Val Ala Pro Gly
465                 470                 475                 480 gag cgc ccc tcc ggc atg ttc gac tcg tcc gtc ctc tgt gag tgc tat         1488
Glu Arg Pro Ser Gly Met Phe Asp Ser Ser Val Leu Cys Glu Cys Tyr
                485                 490                 495 gac gca ggc tgt gct tgg tat gag ctc acg ccc gcc gag act aca gtt         1536
Asp Ala Gly Cys Ala Trp Tyr Glu Leu Thr Pro Ala Glu Thr Thr Val
            500                 505                 510 agg cta cga gcg tac atg aac acc ccg ggg ctt ccc gtg tgc cag gac         1584
Arg Leu Arg Ala Tyr Met Asn Thr Pro Gly Leu Pro Val Cys Gln Asp
        515                 520                 525 cat ctt gaa ttt tgg gag ggc gtc ttt aca ggc ctc act cat ata gat         1632
His Leu Glu Phe Trp Glu Gly Val Phe Thr Gly Leu Thr His Ile Asp
    530                 535                 540 gcc cac ttt cta tcc cag aca aag cag agt ggg gag aac ctt cct tac         1680
Ala His Phe Leu Ser Gln Thr Lys Gln Ser Gly Glu Asn Leu Pro Tyr
545                 550                 555                 560 ctg gta gcg tac caa gcc acc gtg tgc gct agg gct caa gcc cct ccc         1728
Leu Val Ala Tyr Gln Ala Thr Val Cys Ala Arg Ala Gln Ala Pro Pro
                565                 570                 575 cca tcg tgg gac cag atg tgg aag tgt ttg att cgc ctc aag ccc acc         1776
Pro Ser Trp Asp Gln Met Trp Lys Cys Leu Ile Arg Leu Lys Pro Thr
            580                 585                 590 ctc cat ggg cca aca ccc ctg cta tac aga ctg ggc gct gtt cag aat         1824
Leu His Gly Pro Thr Pro Leu Leu Tyr Arg Leu Gly Ala Val Gln Asn
```

-continued

```
        595                 600                 605 gaa atc acc ctg acg cac cca gtc acc aaa tac atc atg aca tgc atg      1872
Glu Ile Thr Leu Thr His Pro Val Thr Lys Tyr Ile Met Thr Cys Met
    610                 615                 620 tcg gcc gac ctg gag gtc gtc acg agc acc tgg gtg ctc gtt ggc ggc      1920
Ser Ala Asp Leu Glu Val Val Thr Ser Thr Trp Val Leu Val Gly Gly
625                 630                 635                 640 gtc ctg gct gct ttg gcc gcg tat tgc ctg tca aca ggc tgc gtg gtc      1968
Val Leu Ala Ala Leu Ala Ala Tyr Cys Leu Ser Thr Gly Cys Val Val
                645                 650                 655 ata gtg ggc agg gtc gtc ttg tcc ggg aag ccg gca atc ata cct gac      2016
Ile Val Gly Arg Val Val Leu Ser Gly Lys Pro Ala Ile Ile Pro Asp
            660                 665                 670 agg gaa gtc ctc tac cga gag ttc gat gag atg gaa gag tgc              2058
Arg Glu Val Leu Tyr Arg Glu Phe Asp Glu Met Glu Glu Cys
        675                 680                 685

<210> SEQ ID NO 3
<211> LENGTH: 686
<212> TYPE: PRT
<213> ORGANISM: Artificial Sequence
<220> FEATURE:
<223> OTHER INFORMATION: Description of Artificial Sequence:
      representative NS3/4a conformational antigen

<400> SEQUENCE: 3

Met Ala Pro Ile Thr Ala Tyr Ala Gln Gln Thr Arg Gly Leu Leu Gly
  1               5                  10                  15

Cys Ile Ile Thr Ser Leu Thr Gly Arg Asp Lys Asn Gln Val Glu Gly
             20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Pro Gln Gly Ser Arg Ser Leu Thr
                 85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Asn Leu
                165                 170                 175

Glu Thr Thr Met Arg Ser Pro Val Phe Thr Asp Asn Ser Ser Pro Pro
            180                 185                 190

Val Val Pro Gln Ser Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
```

-continued

```
                245                 250                 255
Val Arg Thr Ile Thr Thr Gly Ser Pro Ile Thr Tyr Ser Thr Tyr Gly
                    260                 265                 270
Lys Phe Leu Ala Asp Gly Gly Cys Ser Gly Gly Ala Tyr Asp Ile Ile
                275                 280                 285
Ile Cys Asp Glu Cys His Ser Thr Asp Ala Thr Ser Ile Leu Gly Ile
        290                 295                 300
Gly Thr Val Leu Asp Gln Ala Glu Thr Ala Gly Ala Arg Leu Val Val
305                 310                 315                 320
Leu Ala Thr Ala Thr Pro Pro Gly Ser Val Thr Val Pro His Pro Asn
                    325                 330                 335
Ile Glu Glu Val Ala Leu Ser Thr Thr Gly Glu Ile Pro Phe Tyr Gly
                340                 345                 350
Lys Ala Ile Pro Leu Glu Val Ile Lys Gly Gly Arg His Leu Ile Phe
            355                 360                 365
Cys His Ser Lys Lys Lys Cys Asp Glu Leu Ala Ala Lys Leu Val Ala
        370                 375                 380
Leu Gly Ile Asn Ala Val Ala Tyr Tyr Arg Gly Leu Asp Val Ser Val
385                 390                 395                 400
Ile Pro Pro Ile Gly Asp Val Val Val Ala Thr Asp Ala Leu Met
                    405                 410                 415
Thr Gly Tyr Thr Gly Asp Phe Asp Ser Val Ile Asp Cys Asn Thr Cys
                420                 425                 430
Val Thr Gln Thr Val Asp Phe Ser Leu Asp Pro Thr Phe Thr Ile Glu
            435                 440                 445
Thr Ile Thr Leu Pro Gln Asp Ala Val Ser Arg Thr Gln Arg Arg Gly
        450                 455                 460
Arg Thr Gly Arg Gly Lys Pro Gly Ile Tyr Arg Phe Val Ala Pro Gly
465                 470                 475                 480
Glu Arg Pro Ser Gly Met Phe Asp Ser Ser Val Leu Cys Glu Cys Tyr
                    485                 490                 495
Asp Ala Gly Cys Ala Trp Tyr Glu Leu Thr Pro Ala Glu Thr Thr Val
                500                 505                 510
Arg Leu Arg Ala Tyr Met Asn Thr Pro Gly Leu Pro Val Cys Gln Asp
            515                 520                 525
His Leu Glu Phe Trp Glu Gly Val Phe Thr Gly Leu Thr His Ile Asp
        530                 535                 540
Ala His Phe Leu Ser Gln Thr Lys Gln Ser Gly Glu Asn Leu Pro Tyr
545                 550                 555                 560
Leu Val Ala Tyr Gln Ala Thr Val Cys Ala Arg Ala Gln Ala Pro Pro
                    565                 570                 575
Pro Ser Trp Asp Gln Met Trp Lys Cys Leu Ile Arg Leu Lys Pro Thr
                580                 585                 590
Leu His Gly Pro Thr Pro Leu Leu Tyr Arg Leu Gly Ala Val Gln Asn
            595                 600                 605
Glu Ile Thr Leu Thr His Pro Val Thr Lys Tyr Ile Met Thr Cys Met
        610                 615                 620
Ser Ala Asp Leu Glu Val Val Thr Ser Thr Trp Val Leu Val Gly Gly
625                 630                 635                 640
Val Leu Ala Ala Leu Ala Ala Tyr Cys Leu Ser Thr Gly Cys Val Val
                    645                 650                 655
Ile Val Gly Arg Val Val Leu Ser Gly Lys Pro Ala Ile Ile Pro Asp
                660                 665                 670
```

Arg Glu Val Leu Tyr Arg Glu Phe Asp Glu Met Glu Glu Cys
         675                 680                 685

<210> SEQ ID NO 4
<211> LENGTH: 2499
<212> TYPE: DNA
<213> ORGANISM: Artificial Sequence
<220> FEATURE:
<223> OTHER INFORMATION: Description of Artificial Sequence: MEFA 12
<221> NAME/KEY: CDS
<222> LOCATION: (1)..(2487)

<400> SEQUENCE: 4

```
atg gct aca aag gct gtt tgt gtt ttg aag ggt gac ggc cca gtt caa        48
Met Ala Thr Lys Ala Val Cys Val Leu Lys Gly Asp Gly Pro Val Gln
  1               5                  10                  15 ggt att att aac ttc gag cag aag gaa agt aat gga cca gtg aag gtg        96
Gly Ile Ile Asn Phe Glu Gln Lys Glu Ser Asn Gly Pro Val Lys Val
             20                  25                  30 tgg gga agc att aaa gga ctg act gaa ggc ctg cat gga ttc cat gtt       144
Trp Gly Ser Ile Lys Gly Leu Thr Glu Gly Leu His Gly Phe His Val
         35                  40                  45 cat gag ttt gga gat aat aca gca ggc tgt acc agt gca ggt cct cac       192
His Glu Phe Gly Asp Asn Thr Ala Gly Cys Thr Ser Ala Gly Pro His
     50                  55                  60 ttt aat cct cta tcc acg cgt ggt tgc aat tgc tct atc tat ccc ggc       240
Phe Asn Pro Leu Ser Thr Arg Gly Cys Asn Cys Ser Ile Tyr Pro Gly
 65                  70                  75                  80 cat ata acg ggt cac cgc atg gca tgg aag ctt ggt tcc gcc gcc aga       288
His Ile Thr Gly His Arg Met Ala Trp Lys Leu Gly Ser Ala Ala Arg
                 85                  90                  95 act acc tcg ggc ttt gtc tcc ttg ttc gcc cca ggt gcc aaa caa aac       336
Thr Thr Ser Gly Phe Val Ser Leu Phe Ala Pro Gly Ala Lys Gln Asn
            100                 105                 110 gaa act cac gtc acg gga ggc gca gcc gcc cga act acg tct ggg ttg       384
Glu Thr His Val Thr Gly Gly Ala Ala Ala Arg Thr Thr Ser Gly Leu
        115                 120                 125 acc tct ttg ttc tcc cca ggt gcc agc caa aac att caa ttg att act       432
Thr Ser Leu Phe Ser Pro Gly Ala Ser Gln Asn Ile Gln Leu Ile Thr
    130                 135                 140 agt acg gat aac tcc tct cca cca gta gtg ccc cag agc ttc cag gtg       480
Ser Thr Asp Asn Ser Ser Pro Pro Val Val Pro Gln Ser Phe Gln Val
145                 150                 155                 160 gct cac ctc cat gct ccc aca ggc agc ggc aaa agc acc aag gtc ccg       528
Ala His Leu His Ala Pro Thr Gly Ser Gly Lys Ser Thr Lys Val Pro
                165                 170                 175 gct gca tat gca gct cag ggc tat aag gtg cta gta ctc aac ccc tct       576
Ala Ala Tyr Ala Ala Gln Gly Tyr Lys Val Leu Val Leu Asn Pro Ser
            180                 185                 190 gtt gct gca aca ctg ggc ttt ggt gct tac atg tcc aag gct cat ggg       624
Val Ala Ala Thr Leu Gly Phe Gly Ala Tyr Met Ser Lys Ala His Gly
        195                 200                 205 atc gat cct aac atc agg acc ggg gtg aga aca att acc act ggc agc       672
Ile Asp Pro Asn Ile Arg Thr Gly Val Arg Thr Ile Thr Thr Gly Ser
    210                 215                 220 ccc atc acg tac tcc acc tac ggc aag ttc ctt gcc gac ggc ggg tgc       720
Pro Ile Thr Tyr Ser Thr Tyr Gly Lys Phe Leu Ala Asp Gly Gly Cys
225                 230                 235                 240 tcg ggg ggc gct tat gac ata ata att tgt gac gag tgc cac tcc acg       768
Ser Gly Gly Ala Tyr Asp Ile Ile Ile Cys Asp Glu Cys His Ser Thr
                245                 250                 255
```

-continued

| | |
|---|---|
| gat gcc aca tcc atc ttg ggc atc ggc act gtc ctt gac caa gca gag<br>Asp Ala Thr Ser Ile Leu Gly Ile Gly Thr Val Leu Asp Gln Ala Glu<br>260               265               270 | 816 |
| act gcg ggg gcg aga ctg gtt gtg ctc gcc acc gcc acc cct ccg ggc<br>Thr Ala Gly Ala Arg Leu Val Val Leu Ala Thr Ala Thr Pro Pro Gly<br>275                 280               285 | 864 |
| tcc gtc act gtg ccc cat ccc aac atc gag gag gtt gct ctg tcc acc<br>Ser Val Thr Val Pro His Pro Asn Ile Glu Glu Val Ala Leu Ser Thr<br>290               295               300 | 912 |
| acc gga gag atc cct ttt tac ggc aag gct atc ccc ctc gaa gta atc<br>Thr Gly Glu Ile Pro Phe Tyr Gly Lys Ala Ile Pro Leu Glu Val Ile<br>305                 310               315               320 | 960 |
| aag ggg ggg aga cat ctc atc ttc tgt cat tca aag aag aag tgc gac<br>Lys Gly Gly Arg His Leu Ile Phe Cys His Ser Lys Lys Lys Cys Asp<br>325               330               335 | 1008 |
| gaa ctc gcc gca aag ctg gtc gca ttg ggc atc aat gcc gtg gcc tac<br>Glu Leu Ala Ala Lys Leu Val Ala Leu Gly Ile Asn Ala Val Ala Tyr<br>340                 345               350 | 1056 |
| tac cgc ggt ctt gac gtg tcc gtc atc ccg acc agc ggc gat gtt gtc<br>Tyr Arg Gly Leu Asp Val Ser Val Ile Pro Thr Ser Gly Asp Val Val<br>355                 360               365 | 1104 |
| gtc gtg gca acc gat gcc ctc atg acc ggc tat acc ggc gac ttc gac<br>Val Val Ala Thr Asp Ala Leu Met Thr Gly Tyr Thr Gly Asp Phe Asp<br>370               375               380 | 1152 |
| tcg gtg ata gac tgc aat acg tgt gca tgc tcc ggg aag ccg gca atc<br>Ser Val Ile Asp Cys Asn Thr Cys Ala Cys Ser Gly Lys Pro Ala Ile<br>385                 390               395               400 | 1200 |
| ata cct gac agg gaa gtc ctc tac cga gag ttc gat gag atg gaa gag<br>Ile Pro Asp Arg Glu Val Leu Tyr Arg Glu Phe Asp Glu Met Glu Glu<br>405                 410               415 | 1248 |
| tgc tct cag cac tta ccg tac atc gag caa ggg atg atg ctc gcc gag<br>Cys Ser Gln His Leu Pro Tyr Ile Glu Gln Gly Met Met Leu Ala Glu<br>420                 425               430 | 1296 |
| cag ttc aag cag aag gcc ctc ggc ctc tcg cga ggg ggc aag ccg gca<br>Gln Phe Lys Gln Lys Ala Leu Gly Leu Ser Arg Gly Gly Lys Pro Ala<br>435                 440               445 | 1344 |
| atc gtt cca gac aaa gag gtg ttg tat caa caa tac gat gag atg gaa<br>Ile Val Pro Asp Lys Glu Val Leu Tyr Gln Gln Tyr Asp Glu Met Glu<br>450                 455               460 | 1392 |
| gag tgc tca caa gct gcc cca tat atc gaa caa gct cag gta ata gct<br>Glu Cys Ser Gln Ala Ala Pro Tyr Ile Glu Gln Ala Gln Val Ile Ala<br>465                 470               475               480 | 1440 |
| cac cag ttc aag gaa aaa gtc ctt gga ttg atc gat aat gat caa gtg<br>His Gln Phe Lys Glu Lys Val Leu Gly Leu Ile Asp Asn Asp Gln Val<br>485               490               495 | 1488 |
| gtt gtg act cct gac aaa gaa atc tta tat gag gcc ttt gat gag atg<br>Val Val Thr Pro Asp Lys Glu Ile Leu Tyr Glu Ala Phe Asp Glu Met<br>500               505               510 | 1536 |
| gaa gaa tgc gcc tcc aaa gcc gcc ctc att gag gaa ggg cag cgg atg<br>Glu Glu Cys Ala Ser Lys Ala Ala Leu Ile Glu Glu Gly Gln Arg Met<br>515               520               525 | 1584 |
| gcg gag atg ctc aag tct aag ata caa ggc ctc ctc ggg ata ctg cgc<br>Ala Glu Met Leu Lys Ser Lys Ile Gln Gly Leu Leu Gly Ile Leu Arg<br>530               535               540 | 1632 |
| cgg cac gtt ggt cct ggc gag ggg gca gtg cag tgg atg aac cgg ctg<br>Arg His Val Gly Pro Gly Glu Gly Ala Val Gln Trp Met Asn Arg Leu<br>545               550               555               560 | 1680 |
| ata gcc ttc gcc tcc aga ggg aac cat gtt tcc ccc acg cac tac gtt<br>Ile Ala Phe Ala Ser Arg Gly Asn His Val Ser Pro Thr His Tyr Val | 1728 |

```
                    565                 570                 575
ccg tct aga tcc cgg aga ttc gcc cag gcc ctg ccc gtt tgg gcg cgg       1776
Pro Ser Arg Ser Arg Arg Phe Ala Gln Ala Leu Pro Val Trp Ala Arg
            580                 585                 590 ccg gac tat aac ccc ccg cta gtg gag acg tgg aaa aag ccc gac tac       1824
Pro Asp Tyr Asn Pro Pro Leu Val Glu Thr Trp Lys Lys Pro Asp Tyr
        595                 600                 605 gaa cca cct gtg gtc cac ggc aga tct tct cgg aga ttc gcc cag gcc       1872
Glu Pro Pro Val Val His Gly Arg Ser Ser Arg Arg Phe Ala Gln Ala
    610                 615                 620 ctg ccc gtt tgg gcg cgg ccg gac tat aac ccc ccg cta gtg gag acg       1920
Leu Pro Val Trp Ala Arg Pro Asp Tyr Asn Pro Pro Leu Val Glu Thr
625                 630                 635                 640 tgg aaa aag ccc gac tac gaa cca cct gtg gtc cat ggc aga aag acc       1968
Trp Lys Lys Pro Asp Tyr Glu Pro Pro Val Val His Gly Arg Lys Thr
                645                 650                 655 aaa cgt aac acc aac cgg cgg ccg cag gac gtc aag ttc ccg ggt ggc       2016
Lys Arg Asn Thr Asn Arg Arg Pro Gln Asp Val Lys Phe Pro Gly Gly
            660                 665                 670 ggt cag atc gtt ggt gga gtt tac ttg ttg ccg cgc agg ggc cct aga       2064
Gly Gln Ile Val Gly Gly Val Tyr Leu Leu Pro Arg Arg Gly Pro Arg
        675                 680                 685 ttg ggt gtg ctc gcg acg aga aag act tcc cct atc ccc aag gct cgt       2112
Leu Gly Val Leu Ala Thr Arg Lys Thr Ser Pro Ile Pro Lys Ala Arg
    690                 695                 700 cgg ccc gag ggc agg acc tgg gct cag ccc ggt tac cct tgg ccc ctc       2160
Arg Pro Glu Gly Arg Thr Trp Ala Gln Pro Gly Tyr Pro Trp Pro Leu
705                 710                 715                 720 tat ggc aat aag gac aga cgg tct aca ggt aag tcc tgg ggt aag cca       2208
Tyr Gly Asn Lys Asp Arg Arg Ser Thr Gly Lys Ser Trp Gly Lys Pro
                725                 730                 735 ggg tac cct tgg cca aga aag acc aaa cgt aac acc aac cgg cgg ccg       2256
Gly Tyr Pro Trp Pro Arg Lys Thr Lys Arg Asn Thr Asn Arg Arg Pro
            740                 745                 750 cag gac gtc aag ttc ccg ggt ggc ggt cag atc gtt ggt gga gtt tac       2304
Gln Asp Val Lys Phe Pro Gly Gly Gly Gln Ile Val Gly Gly Val Tyr
        755                 760                 765 ttg ttg ccg cgc agg ggc cct aga ttg ggt gtg ctc gcg acg aga aag       2352
Leu Leu Pro Arg Arg Gly Pro Arg Leu Gly Val Leu Ala Thr Arg Lys
    770                 775                 780 act tcc cct atc ccc aag gct cgt cgg ccc gag ggc agg acc tgg gct       2400
Thr Ser Pro Ile Pro Lys Ala Arg Arg Pro Glu Gly Arg Thr Trp Ala
785                 790                 795                 800 cag ccc ggt tac cct tgg ccc ctc tat ggc aat aag gac aga cgg tct       2448
Gln Pro Gly Tyr Pro Trp Pro Leu Tyr Gly Asn Lys Asp Arg Arg Ser
                805                 810                 815 aca ggt aag tcc tgg ggt aag cca ggg tac cct tgg ccc taatgagtcg ac     2499
Thr Gly Lys Ser Trp Gly Lys Pro Gly Tyr Pro Trp Pro
            820                 825

<210> SEQ ID NO 5
<211> LENGTH: 829
<212> TYPE: PRT
<213> ORGANISM: Artificial Sequence
<220> FEATURE:
<223> OTHER INFORMATION: Description of Artificial Sequence:  MEFA 12

<400> SEQUENCE: 5

Met Ala Thr Lys Ala Val Cys Val Leu Lys Gly Asp Gly Pro Val Gln
 1               5                  10                  15
```

```
Gly Ile Ile Asn Phe Glu Gln Lys Glu Ser Asn Gly Pro Val Lys Val
             20                  25                  30

Trp Gly Ser Ile Lys Gly Leu Thr Glu Gly Leu His Gly Phe His Val
         35                  40                  45

His Glu Phe Gly Asp Asn Thr Ala Gly Cys Thr Ser Ala Gly Pro His
     50                  55                  60

Phe Asn Pro Leu Ser Thr Arg Gly Cys Asn Cys Ser Ile Tyr Pro Gly
 65                  70                  75                  80

His Ile Thr Gly His Arg Met Ala Trp Lys Leu Gly Ser Ala Ala Arg
                 85                  90                  95

Thr Thr Ser Gly Phe Val Ser Leu Phe Ala Pro Gly Ala Lys Gln Asn
            100                 105                 110

Glu Thr His Val Thr Gly Ala Ala Ala Arg Thr Thr Ser Gly Leu
            115                 120                 125

Thr Ser Leu Phe Ser Pro Gly Ala Ser Gln Asn Ile Gln Leu Ile Thr
            130                 135                 140

Ser Thr Asp Asn Ser Ser Pro Val Val Pro Gln Ser Phe Gln Val
145                 150                 155                 160

Ala His Leu His Ala Pro Thr Gly Ser Gly Lys Ser Thr Lys Val Pro
                165                 170                 175

Ala Ala Tyr Ala Ala Gln Gly Tyr Lys Val Leu Val Leu Asn Pro Ser
            180                 185                 190

Val Ala Ala Thr Leu Gly Phe Gly Ala Tyr Met Ser Lys Ala His Gly
            195                 200                 205

Ile Asp Pro Asn Ile Arg Thr Gly Val Arg Thr Ile Thr Thr Gly Ser
            210                 215                 220

Pro Ile Thr Tyr Ser Thr Tyr Gly Lys Phe Leu Ala Asp Gly Gly Cys
225                 230                 235                 240

Ser Gly Gly Ala Tyr Asp Ile Ile Cys Asp Glu Cys His Ser Thr
                245                 250                 255

Asp Ala Thr Ser Ile Leu Gly Ile Gly Thr Val Leu Asp Gln Ala Glu
            260                 265                 270

Thr Ala Gly Ala Arg Leu Val Val Leu Ala Thr Ala Thr Pro Pro Gly
            275                 280                 285

Ser Val Thr Val Pro His Pro Asn Ile Glu Glu Val Ala Leu Ser Thr
            290                 295                 300

Thr Gly Glu Ile Pro Phe Tyr Gly Lys Ala Ile Pro Leu Glu Val Ile
305                 310                 315                 320

Lys Gly Gly Arg His Leu Ile Phe Cys His Ser Lys Lys Cys Asp
                325                 330                 335

Glu Leu Ala Ala Lys Leu Val Ala Leu Gly Ile Asn Ala Val Ala Tyr
            340                 345                 350

Tyr Arg Gly Leu Asp Val Ser Val Ile Pro Thr Ser Gly Asp Val Val
            355                 360                 365

Val Val Ala Thr Asp Ala Leu Met Thr Gly Tyr Thr Gly Asp Phe Asp
            370                 375                 380

Ser Val Ile Asp Cys Asn Thr Cys Ala Cys Ser Gly Lys Pro Ala Ile
385                 390                 395                 400

Ile Pro Asp Arg Glu Val Leu Tyr Arg Glu Phe Asp Glu Met Glu Glu
                405                 410                 415

Cys Ser Gln His Leu Pro Tyr Ile Glu Gln Gly Met Met Leu Ala Glu
            420                 425                 430

Gln Phe Lys Gln Lys Ala Leu Gly Leu Ser Arg Gly Gly Lys Pro Ala
```

-continued

```
            435                 440                 445
Ile Val Pro Asp Lys Glu Val Leu Tyr Gln Gln Tyr Asp Glu Met Glu
    450                 455                 460

Glu Cys Ser Gln Ala Ala Pro Tyr Ile Glu Gln Ala Gln Val Ile Ala
465                 470                 475                 480

His Gln Phe Lys Glu Lys Val Leu Gly Leu Ile Asp Asn Asp Gln Val
                485                 490                 495

Val Val Thr Pro Asp Lys Glu Ile Leu Tyr Glu Ala Phe Asp Glu Met
            500                 505                 510

Glu Glu Cys Ala Ser Lys Ala Ala Leu Ile Glu Glu Gly Gln Arg Met
        515                 520                 525

Ala Glu Met Leu Lys Ser Lys Ile Gln Gly Leu Leu Gly Ile Leu Arg
    530                 535                 540

Arg His Val Gly Pro Gly Glu Gly Ala Val Gln Trp Met Asn Arg Leu
545                 550                 555                 560

Ile Ala Phe Ala Ser Arg Gly Asn His Val Ser Pro Thr His Tyr Val
                565                 570                 575

Pro Ser Arg Ser Arg Arg Phe Ala Gln Ala Leu Pro Val Trp Ala Arg
            580                 585                 590

Pro Asp Tyr Asn Pro Pro Leu Val Glu Thr Trp Lys Lys Pro Asp Tyr
        595                 600                 605

Glu Pro Pro Val Val His Gly Arg Ser Arg Arg Phe Ala Gln Ala
    610                 615                 620

Leu Pro Val Trp Ala Arg Pro Asp Tyr Asn Pro Pro Leu Val Glu Thr
625                 630                 635                 640

Trp Lys Lys Pro Asp Tyr Glu Pro Pro Val Val His Gly Arg Lys Thr
                645                 650                 655

Lys Arg Asn Thr Asn Arg Arg Pro Gln Asp Val Lys Phe Pro Gly Gly
            660                 665                 670

Gly Gln Ile Val Gly Gly Val Tyr Leu Leu Pro Arg Arg Gly Pro Arg
        675                 680                 685

Leu Gly Val Leu Ala Thr Arg Lys Thr Ser Pro Ile Pro Lys Ala Arg
    690                 695                 700

Arg Pro Glu Gly Arg Thr Trp Ala Gln Pro Gly Tyr Pro Trp Pro Leu
705                 710                 715                 720

Tyr Gly Asn Lys Asp Arg Arg Ser Thr Gly Lys Ser Trp Gly Lys Pro
                725                 730                 735

Gly Tyr Pro Trp Pro Arg Lys Thr Lys Arg Asn Thr Asn Arg Arg Pro
            740                 745                 750

Gln Asp Val Lys Phe Pro Gly Gly Gly Gln Ile Val Gly Gly Val Tyr
        755                 760                 765

Leu Leu Pro Arg Arg Gly Pro Arg Leu Gly Val Leu Ala Thr Arg Lys
    770                 775                 780

Thr Ser Pro Ile Pro Lys Ala Arg Arg Pro Glu Gly Arg Thr Trp Ala
785                 790                 795                 800

Gln Pro Gly Tyr Pro Trp Pro Leu Tyr Gly Asn Lys Asp Arg Arg Ser
                805                 810                 815

Thr Gly Lys Ser Trp Gly Lys Pro Gly Tyr Pro Trp Pro
            820                 825
```

<210> SEQ ID NO 6
<211> LENGTH: 21
<212> TYPE: PRT
<213> ORGANISM: Artificial Sequence -continued

```
<220> FEATURE:
<223> OTHER INFORMATION: Description of Artificial Sequence:  consensus
      sequence from HCV type 1 genome

<400> SEQUENCE: 6

Gly Ser Ala Ala Arg Thr Thr Ser Gly Phe Val Ser Leu Phe Ala Pro
 1               5                  10                  15

Gly Ala Lys Gln Asn
             20

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence:  sequence

<400> SEQUENCE: 7
acaaaacaaa                                                                10

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence:  NS4A
      peptide

<400> SEQUENCE: 8

Lys Lys Gly Ser Val Val Ile Val Gly Arg Ile Val Leu Ser Gly Lys
 1               5                  10                  15

Pro Ala Ile Ile Pro Lys Lys
             20
```

HCV ANTIGEN/ANTIBODY COMBINATION ASSAY

CROSS-REFERENCE TO RELATED APPLICATIONS

This application is related to provisional patent application serial Nos. 60/212,082, filed Jun. 15, 2000; 60/280,867, filed Apr. 2, 2001; and 60/280,811, filed Apr. 2, 2001, from which applications priority is claimed under 35 USC §119(e)(1) and which applications are incorporated herein by reference in their entireties.

TECHNICAL FIELD

The present invention pertains generally to viral diagnostics. In particular, the invention relates to an antigen/antibody combination assay for accurately diagnosing hepatitis C virus infection.

BACKGROUND OF THE INVENTION

Hepatitis C Virus (HCV) is the principal cause of parenteral non-A, non-B hepatitis (NANBH) which is transmitted largely through blood transfusion and sexual contact. The virus is present in 0.4 to 2.0% of blood donors. Chronic hepatitis develops in about 50% of infections and of these, approximately 20% of infected individuals develop liver cirrhosis which sometimes leads to hepatocellular carcinoma. Accordingly, the study and control of the disease is of medical importance.

HCV was first identified and characterized as a cause of NANBH by Houghten et al. The viral genomic sequence of HCV is known, as are methods for obtaining the sequence. See, e.g., International Publication Nos. WO 89/04669; WO 90/11089; and WO 90/14436. HCV has a 9.5 kb positive-sense, single-stranded RNA genome and is a member of the Flaviridae family of viruses. At least six distinct, but related genotypes of HCV, based on phylogenetic analyses, have been identified (Simmonds et al., *J. Gen. Virol.* (1993) 74:2391–2399). The virus encodes a single polyprotein having more than 3000 amino acid residues (Choo et al., *Science* (1989) 244:359–362; Choo et al., *Proc. Natl. Acad. Sci. USA* (1991) 88:2451–2455; Han et al., *Proc. Natl. Acad. Sci. USA* (1991) 88:1711–1715). The polyprotein is processed co- and post-translationally into both structural and non-structural (NS) proteins.

In particular, as shown in FIG. 1, several proteins are encoded by the HCV genome. The order and nomenclature of the cleavage products of the HCV polyprotein is as follows: $NH_2$-C-E1-E2-p7-NS2-NS3-NS4a-NS4b-NS5a-NS5b-COOH. Initial cleavage of the polyprotein is catalyzed by host proteases which liberate three structural proteins, the N-terminal nucleocapsid protein (termed "core") and two envelope glycoproteins, "E1" (also known as E) and "E2" (also known as E2/NS1), as well as non-structural (NS) proteins that contain the viral enzymes. The NS regions are termed NS2, NS3, NS4 and NS5. NS2 is an integral membrane protein with proteolytic activity. NS2, either alone or in combination with NS3, cleaves the NS2–NS3 sissle bond which in turn generates the NS3 N-terminus and releases a large polyprotein that includes both serine protease and RNA helicase activities. The NS3 protease serves to process the remaining polyprotein. Completion of polyprotein maturation is initiated by autocatalytic cleavage at the NS3–NS4a junction, catalyzed by the NS3 serine protease. Subsequent NS3-mediated cleavages of the HCV polyprotein appear to involve recognition of polyprotein cleavage junctions by an NS3 molecule of another polypeptide. In these reactions, NS3 liberates an NS3 cofactor (NS4a), two proteins (NS4b and NS5a), and an RNA-dependent RNA polymerase (NS5b).

A number of general and specific polypeptides useful as immunological and diagnostic reagents for HCV, derived from the HCV polyprotein, have been described. See, e.g., Houghton et al., European Publication Nos. 318,216 and 388,232; Choo et al., *Science* (1989) 244:359–362; Kuo et al., *Science* (1989) 244:362–364; Houghton et al., *Hepatology* (1991) 14:381–388; Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778. These publications provide an extensive background on HCV generally, as well as on the manufacture and uses of HCV polypeptide immunological reagents. For brevity, therefore, the disclosure of these publications is incorporated herein by reference.

Sensitive, specific methods for screening and identifying carriers of HCV and HCV-contaminated blood or blood products would provide an important advance in medicine. Post-transfusion hepatitis (PTH) occurs in approximately 10% of transfused patients, and HCV has accounted for up to 90% of these cases. Patient care as well as the prevention and transmission of HCV by blood and blood products or by close personal contact require reliable diagnostic and prognostic tools. Accordingly, several assays have been developed for the serodiagnosis of HCV infection. See, e.g., Choo et al., *Science* (1989) 244:359–362; Kuo et al., *Science* (1989) 244:362–364; Choo et al., *Br. Med. Bull.* (1990) 46:423–441; Ebeling et al., *Lancet* (1990) 335:982–983; van der Poel et al., *Lancet* (1990) 335:558–560; van der Poel et al., *Lancet* (1991) 337:317–319; Chien, D. Y., International Publication No. WO 94/01778; Valenzuela et al., International Publication No. WO 97/44469; and Kashiwakuma et al., U.S. Pat. No. 5,871,904.

A significant problem encountered with some serum-based assays is that there is a significant gap between infection and detection of the virus, often exceeding 80 days. This assay gap may create great risk for blood transfusion recipients. To overcome this problem, nucleic acid-based tests (NAT) that detect viral RNA directly, and HCV core antigen tests that assay viral antigen instead of antibody response, have been developed. See, e.g., Kashiwakuma et al., U.S. Pat. No. 5,871,904; Beld et al., *Transfusion* (2000) 40:575–579.

However, there remains a need for sensitive, accurate diagnostic and prognostic tools in order to provide adequate patient care as well as to prevent transmission of HCV by blood and blood products or by close personal contact.

SUMMARY OF THE INVENTION

The present invention is based in part, on the finding that HCV seroconversion antibodies are typically anti-core and anti-NS3 (helicase). Accordingly, the invention provides an HCV core antigen and NS3 antibody combination assay that can detect both HCV antigens and antibodies present in a sample using a single solid matrix.

Accordingly, in one embodiment, the subject invention is directed to an immunoassay solid support comprising at least one HCV anti-core antibody and at least one isolated HCV NS3/4a epitope bound thereto. The antibody and NS3/4a epitope can be any of the herein described molecules. Additionally, the solid support may include any of the multiple epitope fusion antigens described herein, such as the multiple epitope fusion antigen comprising the amino acid sequence depicted in FIGS. 7A–7F.

In certain embodiments, the solid support comprises at least two HCV anti-core antibodies bound thereto. Moreover, the anti-core antibody may be a monoclonal antibody. Additionally, the NS3/4a epitope may be a conformational epitope, such as a conformational NS3/4a epitope comprising the amino acid sequence depicted in FIGS. 4A–4D.

In another embodiment, the invention is directed to an immunoassay solid support comprising at least two HCV anti-core monoclonal antibodies and at least one HCV NS3/4a conformational epitope comprising the amino acid sequence depicted in FIGS. 4A–4D, bound thereto.

In still a further embodiment, the invention is directed to a method of detecting HCV infection in a biological sample. The method comprises: (a) providing an immunoassay solid support as described above; (b) combining a biological sample with the solid support under conditions which allow HCV antigens and antibodies, when present in the biological sample, to bind to the at least one anti-core antibody and the NS3/4a epitope, respectively; (c) adding to the solid support from step (b) under complex forming conditions (i) a first detectably labeled antibody, wherein the first detectably labeled antibody is a detectably labeled HCV anti-core antibody, wherein the labeled anti-core antibody is directed against a different HCV core epitope than the at least one anti-core antibody bound to the solid support; (ii) an antigen that reacts with an HCV antibody from the biological sample reactive with the NS3/4a epitope; and (iii) a second detectably labeled antibody, wherein the second detectably labeled antibody is reactive with the antigen of (ii); and (d) detecting complexes formed between the antibodies and antigens, if any, as an indication of HCV infection in the biological sample. The NS3/4a epitope may be a conformational epitope, such as a conformational epitope having the NS3/4a sequence depicted in FIGS. 4A–4D.

In yet another embodiment, the invention is directed to a method of detecting HCV infection in a biological sample. The method comprises: (a) providing an immunoassay solid support with at least two HCV anti-core antibodies bound thereto, as described above; (b) combining a biological sample with the solid support under conditions which allow HCV antigens and antibodies, when present in the biological sample, to bind to the at least two anti-core antibodies and the NS3/4a epitope, respectively; (c) adding to the solid support from step (b) under complex forming conditions (i) a first detectably labeled antibody, wherein the first detectably labeled antibody is a detectably labeled HCV anti-core antibody, wherein the labeled anti-core antibody is directed against a different HCV core epitope than the anti-core antibodies bound to the solid support; (ii) an epitope from the c33c region of the HCV polyprotein fused to an hSOD amino acid sequence; and (iii) a second detectably labeled antibody, wherein the second detectably labeled antibody is reactive with the hSOD amino acid sequence; and (d) detecting complexes formed between the antibodies and antigens, if any, as an indication of HCV infection in the biological sample. The NS3/4a epitope may be a conformational epitope, such as a conformational epitope having the NS3/4a sequence depicted in FIGS. 4A–4D.

In any of the above embodiments, the anti-core antibody may be directed against an N-terminal region of the HCV core antigen, such as against amino acids 10–53 of HCV, numbered relative to the HCV1 polyprotein sequence, and/or the detectably labeled HCV anti-core antibody may be directed against a C-terminal region of the HCV core antigen, such as amino acids 120–130 of HCV, numbered relative to the HCV1 polyprotein sequence. Moreover, the antigen that reacts with an HCV antibody from the biological sample may be from the NS3 region, such as an epitope from the c33c region of the HCV polyprotein and can be fused with a human superoxide dismutase (hSOD) amino acid sequence. In this embodiment, the second detectably labeled antibody is reactive with the hSOD amino acid sequence.

In another embodiment, the invention is directed to a method of detecting HCV infection in a biological sample. The method comprises: (a) providing an immunoassay solid support including two HCV anti-core monoclonal antibodies and a conformational epitope comprising the amino acid sequence depicted in FIGS. 4A–4D; (b) combining a biological sample with the solid support under conditions which allow HCV antigens and antibodies, when present in the biological sample, to bind to the at least two anti-core antibodies and the NS3/4a conformational epitope, respectively; adding to the solid support from step (b) under complex forming conditions (i) a first detectably labeled antibody, wherein the first detectably labeled antibody is a detectably labeled HCV anti-core antibody, wherein the labeled anti-core antibody is directed against a different HCV core epitope than the at least two anti-core antibodies bound to the solid support; (ii) an epitope from the c33c region of the HCV polyprotein fused to an hSOD amino acid sequence; and (iii) a second detectably labeled antibody, wherein the second detectably labeled antibody is reactive with said hSOD amino acid sequence; detecting complexes formed between the antibodies and antigens, if any, as an indication of HCV infection in the biological sample.

In certain embodiments, the at least two anti-core antibodies are directed against an N-terminal region of the HCV core antigen, such as against amino acids 10–53 of HCV, numbered relative to the HCV1 polyprotein, and the detectably labeled HCV anti-core antibody is directed against a C-terminal region of the HCV core antigen, such as against amino acids 120–130 of HCV, numbered relative to the HCV1 polyprotein sequence.

In another embodiment, the invention is directed to a method of detecting HCV infection in a biological sample. The method comprises: (a) providing an immunoassay solid support which includes a multiple epitope fusion antigen; (b) combining a biological sample with the solid support under conditions which allow HCV antigens and antibodies, when present in the biological sample, to bind to the at least one anti-core antibody, the NS3/4a epitope, and the multiple epitope fusion antigen; (c) adding to the solid support from step (b) under complex forming conditions (i) a first detectably labeled antibody, wherein the first detectably labeled antibody is a detectably labeled HCV anti-core antibody, wherein the labeled anti-core antibody is directed against a different HCV core epitope than the at least one anti-core antibody bound to the solid support; (ii) first and second antigens that react with an HCV antibody from the biological sample reactive with the NS3/4a epitope and the multiple epitope fusion antigen, respectively; and (iii) a second detectably labeled antibody, wherein the second detectably labeled antibody is reactive with the antigens of (ii); (d) detecting complexes formed between the antibodies and antigens, if any, as an indication of HCV infection in the biological sample.

The anti-core antibody may be directed against an N-terminal region of the HCV core antigen and said first detectably labeled HCV anti-core antibody may be directed against a C-terminal region of the HCV core antigen, as described above. Moreover, the first antigen that reacts with an HCV antibody from the biological sample may comprise an epitope from the c33c region of the HCV polyprotein, and may be fused with an hSOD amino acid sequence. In this context, the second detectably labeled antibody is reactive with the hSOD amino acid sequence. Additionally, the second antigen that reacts with an HCV antibody from the biological sample may comprise an epitope from the c22 region of the HCV polyprotein, such as an epitope comprising amino acids $Lys_{10}$ to $Ser_{99}$ of the HCV polyprotein, with a deletion of Arg47 and a substitution of Leu for Trp at position 44, numbered relative to the HCV1 polyprotein sequence. The epitope may be fused with an hSOD amino acid sequence. If so, the second detectably labeled antibody is reactive with the hSOD amino acid sequence. The multiple epitope fusion antigen may comprise the amino acid sequence depicted in FIGS. 7A–7F.

In yet a further embodiment, the invention is directed to a method of detecting HCV infection in a biological sample, said method comprising: (a) providing an immunoassay solid support which comprises two HCV anti-core monoclonal antibodies, an HCV NS3/4a conformational epitope comprising the amino acid sequence depicted in FIGS. 4A–4D, and a multiple epitope fusion antigen comprising the amino acid sequence depicted in FIGS. 7A–7F, bound thereto; (b) combining a biological sample with the solid support under conditions which allow HCV antigens and antibodies, when present in the biological sample, to bind to the at least two anti-core antibodies, the NS3/4a conformational epitope, and the multiple epitope fusion antigen, respectively; (c) adding to the solid support from step (b) under complex forming conditions (i) a first detectably labeled antibody, wherein the first detectably labeled antibody is a detectably labeled HCV anti-core antibody, wherein the labeled anti-core antibody is directed against a different HCV core epitope than the at least two anti-core antibodies bound to the solid support; (ii) an epitope from the c33c region of the HCV polyprotein fused to an hSOD amino acid sequence and an epitope from the c22 region of the HCV polyprotein fused to an hSOD amino acid sequence; and (iii) a second detectably labeled antibody, wherein said second detectably labeled antibody is reactive with said hSOD amino acid sequences; (d) detecting complexes formed between the antibodies and antigens, if any, as an indication of HCV infection in the biological sample.

In this embodiment, the at least two anti-core antibodies may be directed against an N-terminal region of the HCV core antigen, such as against amino acids 10–53 of HCV, numbered relative to the HCV1 polyprotein, and the detectably labeled HCV anti-core antibody is directed against a C-terminal region of the HCV core antigen, such as against amino acids 120–130 of HCV, numbered relative to the HCV1 polyprotein sequence. Moreover, the epitope from the c22 region may comprise amino acids $Lys_{10}$ to $Ser_{99}$ of the HCV polyprotein, with a deletion of Arg47 and a substitution of Leu for Trp at position 44, numbered relative to the HCV1 polyprotein sequence.

In other embodiments, the invention is directed to immunodiagnostic test kits comprising the immunoassay solid support described above, and instructions for conducting the immunodiagnostic test.

In still further embodiments, the invention is directed to methods of producing an immunoassay solid support, comprising: (a) providing a solid support; and (b) binding at least one HCV anti-core antibody, such as one or two or more, and at least one isolated HCV NS3/4a epitope thereto, and optionally, a multiple epitope fusion antigen thereto. The anti-core antibodies, NS3/4a epitopes and multiple epitope fusion antigens are as described above.

In additional embodiments, the invention is directed to a multiple epitope fusion antigen comprising the amino acid sequence depicted in FIGS. 7A–7F, or an amino acid sequence with at least 80% sequence identity, such as 90% or more sequence identity, thereto which reacts specifically with anti-HCV antibodies present in a biological sample from an HCV-infected individual. In certain embodiments, the multiple epitope fusion antigen consists of the amino acid sequence depicted in FIGS. 5A–5F.

In further embodiments, the invention is directed to a polynucleotide comprising a coding sequence for the multiple epitope fusion antigen above, a recombinant vectors comprising the polynucleotides, host cells transformed with the recombinant vectors, and methods of producing a recombinant multiple epitope fusion antigen comprising: (a) providing a population of host cells as above; and (b) culturing the population of cells under conditions whereby the multiple epitope fusion antigen encoded by the coding sequence present in the recombinant vector is expressed.

These and other aspects of the present invention will become evident upon reference to the following detailed description and attached drawings. In addition, various references are set forth herein which describe in more detail certain procedures or compositions, and are therefore incorporated by reference in their entirety.

BRIEF DESCRIPTION OF THE DRAWINGS

FIG. 3 (SEQ ID NO:1) depicts the amino acid sequence of a representative NS3/4a conformational antigen for use in the present assays. The bolded alanine at position 182 is substituted for the native serine normally present at this position.

FIGS. 4A through 4D depict the DNA (SEQ ID NO:2) and corresponding amino acid (SEQ ID NO:3) sequence of another representative NS3/4a conformational antigen for use in the present assays. The amino acids at positions 403 and 404 of FIGS. 4A through 4D represent substitutions of Pro for Thr, and Ile for Ser, of the native amino acid sequence of HCV-1.

FIG. 6 is a diagrammatic representation of MEFA 12.

FIGS. 7A–7F depict the DNA (SEQ ID NO:4) and corresponding amino acid (SEQ ID NO:5) sequence of MEFA 12.

DETAILED DESCRIPTION OF THE INVENTION

Figure 1:
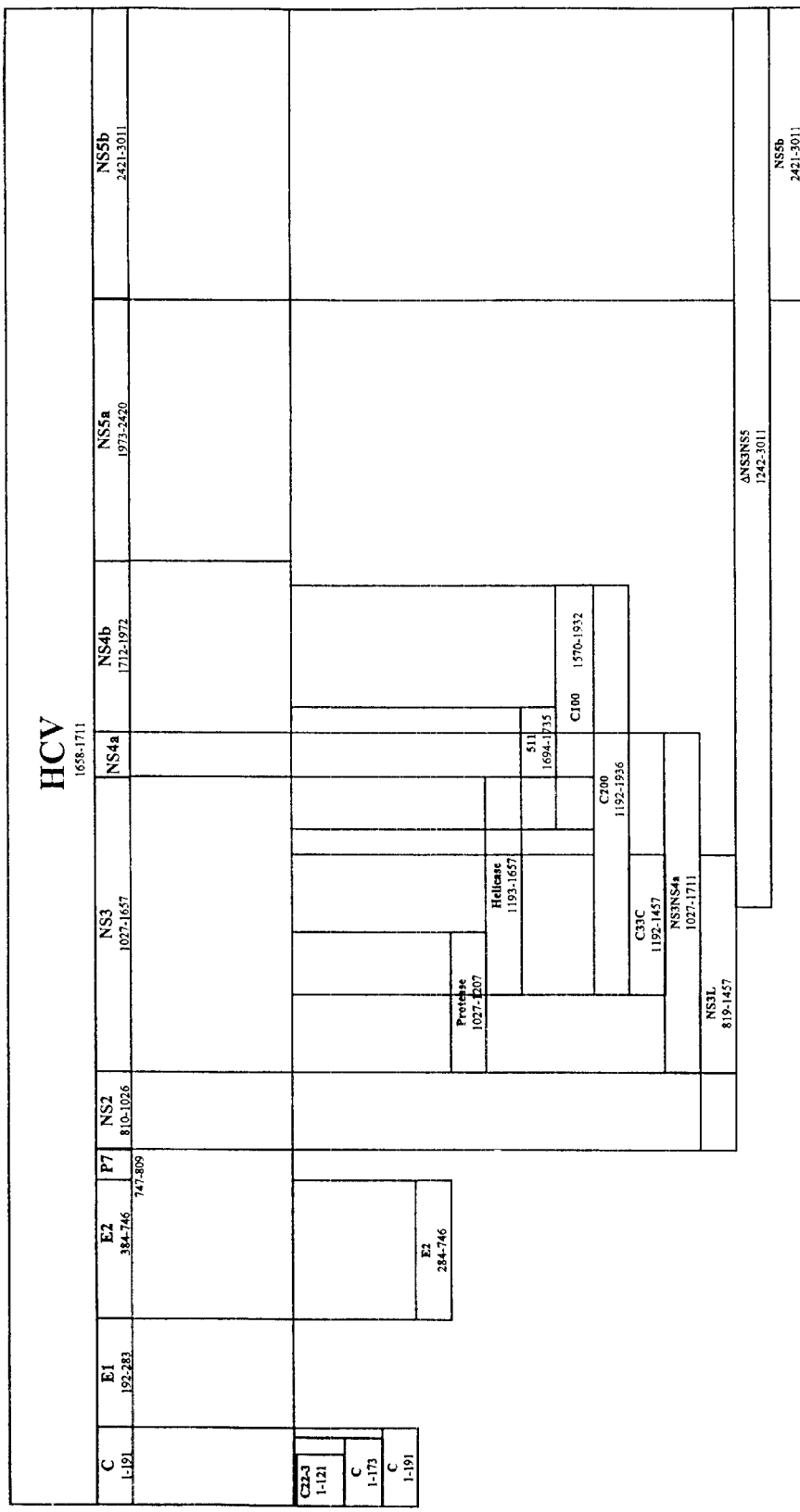
FIG. 1 is a diagrammatic representation of the HCV genome, depicting the various regions of the polyprotein from which the present assay reagents (proteins and antibodies) are derived.
Figure 2:
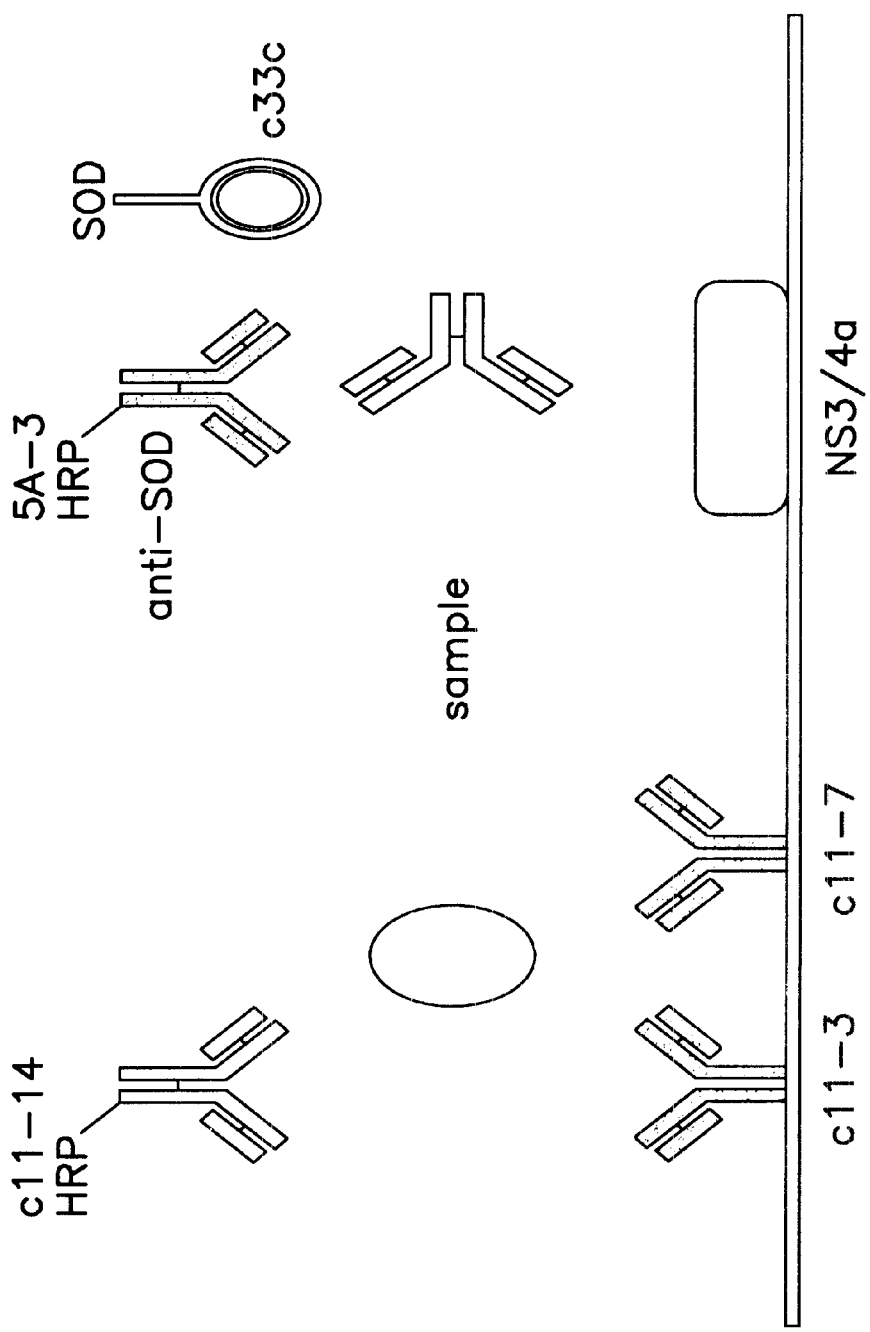
FIG. 2 is a schematic drawing of a representative antibody/antigen combination assay under the invention.

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental*

*Virology*, 2nd Edition, vol. I & II (B. N. Fields and D. M. Knipe, eds.); *Handbook of Experimental Immunology*, Vols. I–IV (D. M. Weir and C. C. Blackwell eds., Blackwell Scientific Publications); T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

An HCV polypeptide is a polypeptide, as defined above, derived from the HCV polyprotein. The polypeptide need not be physically derived from HCV, but may be synthetically or recombinantly produced. Moreover, the polypeptide may be derived from any of the various HCV strains, such as from strains 1, 2, 3 or 4 of HCV. A number of conserved and variable regions are known between these strains and, in general, the amino acid sequences of epitopes derived from these regions will have a high degree of sequence homology, e.g., amino acid sequence homology of more than 30%, preferably more than 40%, when the two sequences are aligned. Thus, for example, the term "NS3/4a" polypeptide refers to native NS3/4a from any of the various HCV strains, as well as NS3/4a analogs, muteins and immunogenic fragments, as defined further below. The complete genotypes of many of these strains are known. See, e.g., U.S. Pat. No. 6,150,087 and GenBank Accession Nos. AJ238800 and AJ238799.

The terms "analog" and "mutein" refer to biologically active derivatives of the reference molecule, or fragments of such derivatives, that retain desired activity, such as immunoreactivity in the assays described herein. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to peptides having one or more peptide mimics ("peptoids"), such as those described in International Publication No. WO 91/04282. Preferably, the analog or mutein has at least the same immunoactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5–10 conservative or non-conservative amino acid substitutions, or even up to about 15–25 conservative or non-conservative amino acid substitutions, or any integer between 5–25, so long as the desired function of the molecule remains intact. One of skill in the art may readily determine regions of the molecule of interest that can tolerate change by reference to Hopp/Woods and Kyte-Doolittle plots, well known in the art.

By "fragment" is intended a polypeptide consisting of only a part of the intact full-length polypeptide sequence and structure. The fragment can include a C-terminal deletion and/or an N-terminal deletion of the native polypeptide. An "immunogenic fragment" of a particular HCV protein will generally include at least about 5–10 contiguous amino acid residues of the full-length molecule, preferably at least about 15–25 contiguous amino acid residues of the full-length molecule, and most preferably at least about 20–50 or more contiguous amino acid residues of the full-length molecule, that define an epitope, or any integer between 5 amino acids and the full-length sequence, provided that the fragment in question retains immunoreactivity in the assays described herein. For example, preferred immunogenic fragments, include but are not limited to fragments of HCV core that comprise, e.g., amino acids 10–45, 10–53, 67–88, and 120–130 of the polyprotein, epitope 5-1-1 (in the NS3 region of the viral genome) as well as defined epitopes derived from the E1, E2, c33c (NS3), c100 (NS4), NS3/4a and NS5 regions of the HCV polyprotein, as well as any of the other various epitopes identified from the HCV polyprotein. See, e.g., Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778; U.S. Pat. Nos. 6,150,087 and 6,121,020, all of which are incorporated by reference herein.

The term "epitope" as used herein refers to a sequence of at least about 3 to 5, preferably about 5 to 10 or 15, and not more than about 1,000 amino acids (or any integer therebetween), which define a sequence that by itself or as part of a larger sequence, binds to an antibody generated in response to such sequence. There is no critical upper limit to the length of the fragment, which may comprise nearly the full-length of the protein sequence, or even a fusion protein comprising two or more epitopes from the HCV polyprotein. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998–4002; Geysen et al. (1985) *Proc. Natl. Acad. Sci. USA* 82:178–182; Geysen et al. (1986) *Molec. Immunol.* 23:709–715, all incorporated herein by reference in their entireties. Using such techniques, a number of epitopes of HCV have been identified. See, e.g., Chien et al., *Viral Hepatitis and Liver Disease* (1994) pp. 320–324, and further below. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824–3828 for determining antigenicity profiles, and the Kyte-Doolittle technique, Kyte et al., *J. Mol. Biol.* (1982) 157:105–132 for hydropathy plots.

As used herein, the term "conformational epitope" refers to a portion of a full-length protein, or an analog or mutein thereof, having structural features native to the amino acid sequence encoding the epitope within the full-length natural protein. Native structural features include, but are not limited to, glycosylation and three dimensional structure. The length of the epitope defining sequence can be subject to wide variations as these epitopes are believed to be formed by the three-dimensional shape of the antigen (e.g., folding). Thus, amino acids defining the epitope can be relatively few in number, but widely dispersed along the length of the molecule (or even on different molecules in the case of dimers, etc.), being brought into correct epitope conformation via folding. The portions of the antigen between the residues defining the epitope may not be critical to the conformational structure of the epitope. For example, deletion or substitution of these intervening sequences may not affect the conformational epitope provided sequences critical to epitope conformation are maintained (e.g., cysteines involved in disulfide bonding, glycosylation sites, etc.).

Conformational epitopes present in the NS3/4a region are readily identified using methods discussed above. Moreover, the presence or absence of a conformational epitope in a given polypeptide can be readily determined through screening the antigen of interest with an antibody (polyclonal serum or monoclonal to the conformational epitope) and comparing its reactivity to that of a denatured version of the antigen which retains only linear epitopes (if any). In such screening using polyclonal antibodies, it may be advantageous to absorb the polyclonal serum first with the denatured antigen and see if it retains antibodies to the antigen of interest. Additionally, in the case of NS3/4a, a molecule which preserves the native conformation will also have protease and, optionally, helicase enzymatic activities. Such activities can be detected using enzymatic assays, as described further below.

Preferably, a conformational epitope is produced recombinantly and is expressed in a cell from which it is extractable under conditions which preserve its desired structural features, e.g. without denaturation of the epitope. Such cells include bacteria, yeast, insect, and mammalian cells. Expression and isolation of recombinant conformational epitopes from the HCV polyprotein are described in e.g., International Publication Nos. WO 96/04301, WO 94/01778, WO 95/33053, WO 92/08734, which applications are herein incorporated by reference in their entirety. Alternatively, it is possible to express the antigens and further renature the protein after recovery. It is also understood that chemical synthesis may also provide conformational antigen mimitopes that cross-react with the "native" antigen's conformational epitope.

The term "multiple epitope fusion antigen" or "MEFA" as used herein intends a polypeptide in which multiple HCV antigens are part of a single, continuous chain of amino acids, which chain does not occur in nature. The HCV antigens may be connected directly to each other by peptide bonds or may be separated by intervening amino acid sequences. The fusion antigens may also contain sequences exogenous to the HCV polyprotein. Moreover, the HCV sequences present may be from multiple genotypes and/or isolates of HCV. Examples of particular MEFAs for use in the present immunoassays are detailed in, e.g., International Publication No. WO 97/44469, incorporated herein by reference in its entirety, and are described further below.

An "antibody" intends a molecule that, through chemical or physical means, specifically binds to a polypeptide of interest. Thus, an HCV core antibody is a molecule that specifically binds to the HCV core protein. The term "antibody" as used herein includes antibodies obtained from both polyclonal and monoclonal preparations, as well as, the following: hybrid (chimeric) antibody molecules (see, for example, Winter et al. (1991) *Nature* 349:293–299; and U.S. Pat. No. 4,816,567); F(ab')$_2$ and F(ab) fragments; Fv molecules (non-covalent heterodimers, see, for example, Inbar et al. (1972) *Proc Natl Acad Sci USA* 69:2659–2662; and Ehrlich et al. (1980) *Biochem* 19:4091–4096); single-chain Fv molecules (sFv) (see, for example, Huston et al. (1988) *Proc Natl Acad Sci USA* 85:5879–5883); dimeric and trimeric antibody fragment constructs; minibodies (see, e.g., Pack et al. (1992) *Biochem* 31:1579–1584; Cumber et al. (1992) *J Immunology* 149B:120–126); humanized antibody molecules (see, for example, Riechmann et al. (1988) *Nature* 332:323–327; Verhoeyan et al. (1988) *Science* 239:1534–1536; and U.K. Patent Publication No. GB 2,276, 169, published Sep. 21, 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human rather than murine hybridomas. See, e.g., Cote, et al. *Monclonal Antibodies and Cancer Therapy*, Alan R. Liss, 1985, p. 77.

A "recombinant" protein is a protein which retains the desired activity and which has been prepared by recombinant DNA techniques as described herein. In general, the gene of interest is cloned and then expressed in transformed organisms, as described further below. The host organism expresses the foreign gene to produce the protein under expression conditions.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

By "equivalent antigenic determinant" is meant an antigenic determinant from different sub-species or strains of HCV, such as from strains 1, 2, or 3 of HCV. More specifically, epitopes are known, such as 5-1-1, and such epitopes vary between the strains 1, 2, and 3. Thus, the epitope 5-1-1 from the three different strains are equivalent antigenic determinants and thus are "copies" even though their sequences are not identical. In general the amino acid sequences of equivalent antigenic determinants will have a high degree of sequence homology, e.g., amino acid sequence homology of more than 30%, preferably more than 40%, when the two sequences are aligned.

"Homology" refers to the percent similarity between two polynucleotide or two polypeptide moieties. Two DNA, or two polypeptide sequences are "substantially homologous" to each other when the sequences exhibit at least about 50% , preferably at least about 75%, more preferably at least about 80%–85%, preferably at least about 90%, and most preferably at least about 95%–98% sequence similarity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of similarity and identity, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman *Advances in Appl. Math.* 2:482–489, 1981 for peptide analysis. Programs for determining nucleotide sequence similarity and identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent similarity of a particular nucleotide sequence to a reference sequence can be determined using the homology algorithm of Smith and Waterman with a default scoring table and a gap penalty of six nucleotide positions.

Another method of establishing percent similarity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence similarity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter= none; strand=both; cutoff=60; expect=10; Matrix= BLOSUM62; Descriptions=50 sequences; sort by=HIGH SCORE; Databases=non-redundant, GenBank+EMBL+ DDBJ+PDB+GenBank CDS translations+Swiss protein+ Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

A "coding sequence" or a sequence which "encodes" a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

A "host cell" is a cell which has been transformed, or is capable of transformation, by an exogenous DNA sequence.

"Common solid support" intends a single solid matrix to which the HCV polypeptides used in the subject immunoassays are bound covalently or by noncovalent means such as hydrophobic adsorption.

"Immunologically reactive" means that the antigen in question will react specifically with anti-HCV antibodies present in a biological sample from an HCV-infected individual.

"Immune complex" intends the combination formed when an antibody binds to an epitope on an antigen.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, strepavidin or haptens) and the like. The term "fluorescer refers" to a substance or a portion thereof which is capable of exhibiting fluorescence in the detectable range. Particular examples of labels which may be used under the invention include, but are not limited to, horse radish peroxidase (HRP), fluorescein, FITC, rhodamine, dansyl, umbelliferone, dimethyl acridinium ester (DMAE), Texas red, luminol, NADPH and $\alpha$-$\beta$-galactosidase.

II. Modes of Carrying out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As noted above, the present invention is based on the discovery of novel diagnostic methods for accurately detecting early HCV infection. The methods rely on the identification and use of highly immunogenic HCV antibodies and antigens which are present during the early stages of HCV seroconversion, thereby increasing detection accuracy and reducing the incidence of false results. The methods can be conveniently practiced in a single assay format.

More particularly, the assay is conducted on a solid support to which has been bound one or more HCV anti-core antibodies (directed against either the same or different HCV core epitopes) and an epitope derived from the NS3/4a region of the HCV polyprotein. Examples of particular anti-core antibodies useful in the present invention include, but are not limited to, antibody molecules such as monoclonal antibodies, directed against epitopes in the core region found between amino acids 10–53; amino acids 10–45; amino acids 67–88; amino acids 120–130, or antibodies directed against any of the core epitopes identified in, e.g., Houghton et al., U.S. Pat. No. 5,350,671; Chien et al., Proc. Natl. Acad. Sci. USA (1992) 89:10011–10015; Chien et al., J. Gastroent. Hepatol. (1993) 8:S33–39; Chien et al., International Publication No. WO 93/00365; Chien, D. Y., International Publication No. WO 94/01778; and commonly owned, allowed U.S. patent application Serial Nos. 08/403,590 and 08/444,818, the disclosures of which are incorporated herein by reference in their entireties.

The NS3/4a region of the HCV polyprotein has been described and the amino acid sequence and overall structure of the protein are disclosed in, e.g., Yao et al., *Structure* (November 1999) 7:1353–1363; Sali et al., *Biochem.* (1998) 37:3392–3401; and Bartenschlager, R., *J. Viral Hepat.* (1999) 6:165–181. See, also, Dasmahapatra et al., U.S. Pat. No. 5,843,752, incorporated herein by reference in its entirety. The subject immunoassays utilize at least one conformational epitope derived from the NS3/4a region that exists in the conformation as found in the naturally occurring HCV particle or its infective product, as evidenced by the preservation of protease and, optionally, helicase enzymatic activities normally displayed by the NS3/4a gene product and/or immunoreactivity of the antigen with antibodies in a biological sample from an HCV-infected subject, and a loss of the epitope's immunoreactivity upon denaturation of the antigen. For example, the conformational epitope can be disrupted by heating, changing the pH to extremely acid or basic, or by adding known organic denaturants, such as dithiothreitol (DTT) or an appropriate detergent. See, e.g., *Protein Purification Methods, a practical approach* (E. L. V. Harris and S. Angal eds., IRL Press) and the denatured product compared to the product which is not treated as above.

Protease and helicase activity may be determined using standard enzyme assays well known in the art. For example, protease activity may be determined using assays well known in the art. See, e.g., Takeshita et al., *Anal. Biochem.* (1997) 247:242–246; Kakiuchi et al., *J. Biochem.* (1997) 122:749–755; Sali et al., *Biochemistry* (1998) 37:3392–3401; Cho et al., *J. Virol. Meth.* (1998) 72:109–115; Cerretani et al., *Anal. Biochem.* (1999) 266:192–197; Zhang et al., *Anal. Biochem.* (1999) 270:268–275; Kakiuchi et al., *J. Virol. Meth.* (1999) 80:77–84; Fowler et al., *J. Biomol. Screen.* (2000) 5:153–158; and Kim et al., *Anal. Biochem.* (2000) 284:42–48. A particularly convenient assay for testing protease activity is set forth in the examples below.

Similarly, helicase activity assays are well known in the art and helicase activity of an NS3/4a epitope may be determined using, for example, an ELISA assay, as described in, e.g., Hsu et al., *Biochem. Biophys. Res. Commun.* (1998) 253:594–599; a scintillation proximity assay system, as described in Kyono et al., *Anal. Biochem.* (1998) 257:120–126; high throughput screening assays as described in, e.g., Hicham et al., *Antiviral Res.* (2000) 46:181–193 and Kwong et al., *Methods Mol. Med.* (2000) 24:97–116; as well as by other assay methods known in the art. See, e.g., Khu et al., *J. Virol.* (2001) 75:205–214; Utama et al., *Virology* (2000) 273:316–324; Paolini et al., *J. Gen. Virol.* (2000) 81:1335–1345; Preugschat et al., *Biochemistry* (2000) 39:5174–5183; Preugschat et al., *Methods Mol. Med.* (1998) 19:353–364; and Hesson et al., *Biochemistry* (2000) 39:2619–2625.

The length of the antigen is sufficient to maintain an immunoreactive conformational epitope. Often, the polypeptide containing the antigen used will be almost full-length, however, the polypeptide may also be truncated to, for example, increase solubility or to improve secretion. Generally, the conformational epitope found in NS3/4a is expressed as a recombinant polypeptide in a cell and this polypeptide provides the epitope in a desired form, as described in detail below.

Representative amino acid sequences for NS3/4a polypeptides are shown in FIG. 3 and FIGS. 4A through 4D. The bolded alanine occurring at position 182 of FIG. 3 is substituted for the native serine found at this position in order to prevent autocatalyisis of the molecule that might otherwise occur. The amino acid sequence shown at positions 2–686 of FIGS. 4A through 4D corresponds to amino acid positions 1027–1711 of HCV-1. An initiator codon (ATG) coding for Met, is shown as position 1. Additionally, the Thr normally occurring at position 1428 of HCV-1 (amino acid position 403 of FIG. 4) is mutated to Pro, and the Ser normally occurring at position 1429 of HCV-1 (amino acid position 404 of FIG. 4) is mutated to Ile. However, either the native sequence, with or without an N-terminal Met, the depicted analog, with or without the N-terminal Met, or other analogs and fragments can be used in the subject assays, so long as the epitope is produced using a method that retains or reinstates its native conformation such that protease activity, and optionally, helicase activity is retained. Dasmahapatra et al., U.S. Pat. No. 5,843,752 and Zhang et al., U.S. Pat. No. 5,990,276, both describe analogs of NS3/4a.

The NS3 protease of NS3/4a is found at about positions 1027–1207, numbered relative to HCV-1, positions 2–182 of FIG. 4. The structure of the NS3 protease and active site are known. See, e.g., De Francesco et al., *Antivir. Ther.* (1998) 3:99–109; Koch et al., *Biochemistry* (2001) 40:631–640. Changes to the native sequence that will normally be tolerated will be those outside of the active site of the molecule. Particularly, it is desirable to maintain amino acids 1- or 2–155 of FIG. 4, with little or only conservative substitutions. Amino acids occurring beyond 155 will tolerate greater changes. Additionally, if fragments of the NS3/4a sequence found in FIG. 4 are used, these fragments will generally include at least amino acids 1- or 2–155, preferably amino acids 1- or 2–175, and most preferably amino acids 1- or 2–182, with or without the N-terminal Met. The helicase domain is found at about positions 1193–1657 of HCV-1 (positions 207–632 of FIG. 4). Thus, if helicase activity is desired, this portion of the molecule will be maintained with little or only conservative changes. One of skill in the art can readily determine other regions that will tolerate change based on the known structure of NS3/4a.

The solid support may also comprise other antigens. For example, multiple epitope fusion antigens (termed "MEFAs"), as described in International Publication No. WO 97/44469, may be bound to the solid support for use in the subject assays. Such MEFAs include multiple epitopes derived from two or more of the various viral regions shown in FIG. 1 and Table 1. In particular, as shown in FIG. 1 and Table 1, An HCV polyprotein, upon cleavage, produces at least ten distinct products, in the order of $NH_2$-Core-E1-E2-p7-NS2-NS3-NS4a-NS4b-NS5a-NS5b-COOH. The core polypeptide occurs at positions 1–191, numbered relative to HCV-1 (see, Choo et al. (1991) *Proc. Natl. Acad. Sci. USA* 88:2451–2455, for the HCV-1 genome). This polypeptide is further processed to produce an HCV polypeptide with approximately amino acids 1–173. The envelope polypeptides, E1 and E2, occur at about positions 192–383 and 384–746, respectively. The P7 domain is found at about positions 747–809. NS2 is an integral membrane protein with proteolytic activity and is found at about positions 810–1026 of the polyprotein. NS2, either alone or in combination with NS3 (found at about positions 1027–1657), cleaves the NS2–NS3 sissle bond which in turn generates the NS3 N-terminus and releases a large polyprotein that includes both serine protease and RNA helicase activities. The NS3 protease, found at about positions 1027–1207, serves to process the remaining polyprotein. The helicase activity is found at about positions 1193–1657. Completion of polyprotein maturation is initiated by autocatalytic cleavage at the NS3–NS4a junction, catalyzed by the NS3 serine protease. Subsequent NS3-mediated cleavages of the HCV polyprotein appear to involve recognition of polyprotein cleavage junctions by an NS3 molecule of another polypeptide. In these reactions, NS3 liberates an NS3 cofactor (NS4a, found about positions 1658–1711), two proteins (NS4b found at about positions 1712–1972, and NS5a found at about positions 1973–2420), and an RNA-dependent RNA polymerase (NS5b found at about positions 2421–3011).

TABLE 1

| Domain | Approximate Boundaries* |
|---|---|
| C (core) | 1–191 |
| E1 | 192–383 |
| E2 | 384–746 |
| P7 | 747–809 |
| NS2 | 810–1026 |
| NS3 | 1027–1657 |
| NS4a | 1658–1711 |
| NS4b | 1712–1972 |
| NS5a | 1973–2420 |
| NS5b | 2421–3011 |

*Numbered relative to HCV-1. See, Choo et al. (1991) Proc. Natl. Acad. Sci. USA 88: 2451–2455.

The multiple HCV antigens are part of a single, continuous chain of amino acids, which chain does not occur in nature. Thus, the linear order of the epitopes is different than their linear order in the genome in which they occur. The linear order of the sequences of the MEFAs for use herein is preferably arranged for optimum antigenicity. Preferably, the epitopes are from more than one HCV strain, thus providing the added ability to detect multiple strains of HCV in a single assay. Thus, the MEFAs for use herein may comprise various immunogenic regions derived from the polyprotein described above. Moreover, a protein resulting from a frameshift in the core region of the polyprotein, such as described in International Publication No. WO 99/63941, may be used in the MEFAs. If desired, at least 2, 3, 4, 5, 6, 7, 8, 9, or 10 or more of one or more epitopes derived from the HCV polyprotein may occur in the fusion protein.

For example, epitopes derived from, e.g., the hypervariable region of E2, such as a region spanning amino acids 384–410 or 390–410, can be included in the MEFA antigen. A particularly effective E2 epitope is one which includes a consensus sequence derived from this region, such as the consensus sequence Gly-Ser-Ala-Ala-Arg-Thr-Thr-Ser-Gly-Phe-Val-Ser-Leu-Phe-Ala-Pro-Gly-Ala-Lys-Gln-Asn (SEQ ID NO:6), which represents a consensus sequence for amino acids 390–410 of the HCV type 1 genome. A representative E2 epitope present in a MEFA of the invention can comprise a hybrid epitope spanning amino acids 390–444. Such a hybrid E2 epitope can include a consensus sequence representing amino acids 390–410 fused to the native amino acid sequence for amino acids 411–444 of HCV E2.

Additionally, the antigens may be derived from various HCV strains. Multiple viral strains of HCV are known, and epitopes derived from any of these strains can be used in a fusion protein. It is well known that any given species of organism varies from one individual organism to another and further that a given organism such as a virus can have a number of different strains. For example, as explained above, HCV includes at least 6 genotypes. Each of these genotypes includes equivalent antigenic determinants. More specifically, each strain includes a number of antigenic determinants that are present on all strains of the virus but are slightly different from one viral strain to another. For example, HCV includes the antigenic determinant known as 5-1-1 (See, FIG. 1). This particular antigenic determinant appears in three different forms on the three different viral strains of HCV. Accordingly, in a preferred embodiment of the invention all three forms of 5-1-1 appear on the multiple epitope fusion antigen used in the subject immunoassays. Similarly, equivalent antigenic determinants from the core region of different HCV strains may also be present. In general, equivalent antigenic determinants have a high degree of homology in terms of amino acid sequence which degree of homology is generally 30% or more, preferably 40% or more, when aligned. The multiple copy epitope of the present invention can also include multiple copies which are exact copies of the same epitope.

Representative MEFAs for use with the present assays are described in International Publication No. WO 97/44469. Additional representative MEFAs for use herein include those termed MEFA 12, MEFA 13 and MEFA 13.1. It is to be understood that these MEFAs are merely representative and other epitopes derived from the HCV genome will also find use with the present assays and may be incorporated into these or other MEFAs.

The DNA sequence and corresponding amino acid sequence of MEFA 12 is shown in FIGS. 7A through 7F. The general structural formula for MEFA 12 is shown in FIG. 6 and is as follows: hSOD-E1(type 1)-E2 HVR consensus (type 1a)-E2 HVR consensus(types 1 and 2)-c33c short(type 1)-5-1-1(type 1)-5-1-1(type 3)-5-1-1(type 2)-c100(type 1)-NS5(type 1)-NS5(type 1)-core(types 1+2)-core(types 1+2). This multiple copy epitope includes the following amino acid sequence, numbered relative to HCV-1 (the numbering of the amino acids set forth below follows the numbering designation provided in Choo, et al. (1991) *Proc. Natl. Acad. Sci. USA* 88:2451–2455, in which amino acid #1 is the first methionine encoded by the coding sequence of the core region): amino acids 1–69 of superoxide dismutase (SOD, used to enhance recombinant expression of the protein); amino acids 303 to 320 of the polyprotein from the E1 region; amino acids 390 to 410 of the polyprotein, representing a consensus sequence for the hypervariable region of HCV-1a E2; amino acids 384 to 414 of the polyprotein from region E2, representing a consensus sequence for the E2 hypervariable regions of HCV-1 and HCV-2; amino acids 1211–1457 of the HCV-1 polyprotein which define the helicase; three copies of an epitope from 5-1-1, amino acids 1689–1735, one from HCV-1, one from HCV-3 and one from HCV-2, which copies are equivalent antigenic determinants from the three different viral strains of HCV; HCV polypeptide C100 of HCV-1, amino acids 1901–1936 of the polyprotein; two exact copies of an epitope from the NS5 region of HCV-1, each with amino acids 2278 to 2313 of the HCV polyprotein; and two copies of three epitopes from the core region, two from HCV-1 and one from HCV-2, which copies are equivalent antigenic determinants represented by amino acids 9 to 53 and 64–88 of HCV-1 and 67–84 of HCV-2.

Table 2 shows the amino acid positions of the various epitopes in MEFA 12 with reference to FIGS. 7A through 7F herein. The numbering in the tables is relative to HCV-1. See, Choo et al. (1991) *Proc. Natl. Acad. Sci. USA* 88:2451–2455. MEFAs 13 and 13.1 also share the general formula specified above for MEFA 12, with modifications as indicated in Tables 3 and 4, respectively.

TABLE 2

MEFA 12

| mefa aa# | 5' end site | epitope | hcv aa# | strain |
|---|---|---|---|---|
| 1–69* | Nco1 | hSOD | | |
| 72–89 | MluI | E1 | 303–320 | 1 |
| 92–112 | Hind111 | E2 HVR1a consensus | 390–410 | 1 |
| 113–143 | | E2 HVR1 + 2 consensus | 384–414 | 1, 2 |
| 146–392 | SpeI | C33C short | 1211–1457 | 1 |
| 395–441 | SphI | 5-1-1 | 1689–1735 | 1 |
| 444–490 | NruI | 5-1-1 | 1689–1735 | 3 |
| 493–539 | ClaI | 5-1-1 | 1689–1735 | 2 |
| 542–577 | AvaI | C100 | 1901–1936 | 1 |
| 580–615 | XbaI | NS5 | 2278–2313 | 1 |
| 618–653 | BglII | NS5 | 2278–2313 | 1 |
| 654–741 | NcoI | core | 9–53, R47L | 1 |
| | | epitopes | 64–88 | 1 |
| | | | 67–84 | 2 |
| 742–829 | BalI | core | 9–53, R47L | 1 |
| | | epitopes | 64–88 | 1 |
| | | | 67–84 | 2 |

*The SOD protein is truncated so that so that the detection conjugate, an HRP-labeled anti-SOD antibody does not bind the MEFA. The core epitope is mutated to prevent the antibodies to HCV core, used in detection, from binding to the MEFA.

TABLE 3

MEFA 13

| mefa aa# | 5' end site | epitope | hcv aa# | strain |
|---|---|---|---|---|
| 1–156 | Nco1 | mutated hSOD (aa 70–72, ALA) | | |
| 161–178 | MluI | E1 | 303–320 | 1 |
| 181–201 | Hind111 | E2 HVR1a consensus | 390–410 | 1 |
| 202–232 | | E2 HVR1 + 2 consensus | 384–414 | 1, 2 |
| 235–451 | | C33C short | 1211–1457 | 1 |
| 454–500 | HindIII | 5-1-1 PImut* | 1689–1735 | 1 |
| 503–549 | NruI | 5-1-1 PImut* | 1689–1735 | 3 |
| 552–598 | ClaI | 5-1-1 PImut* | 1689–1735 | 2 |
| 601–636 | AvaI | C100 | 1901–1936 | 1 |
| 639–674 | XbaI | NS5 | 2278–2313 | 1 |
| 677–712 | BglII | NS5 | 2278–2313 | 1 |
| 713–800 | | core | 9–53, R47L | 1 |
| | | epitopes | 64–88 | 1 |
| | | | 67–84 | 2 |
| 801–888 | | core | 9–53, R47L | 1 |
| | | epitopes | 64–88 | 1 |
| | | | 67–84 | 2 |

*The 5-1-1 epitopes are modified by eliminating possible cleavage sites (CS or CA) targeted by the NS3/4a recombinant protein. Instead of CS or CA, the sequence has been changed to PI. Additionally, the SOD protein is mutated so that the detection conjugate, an HRP-labeled anti-SOD antibody does not bind the MEFA. The core epitope is mutated to prevent the antibodies to HCV core, used in detection, from binding to the MEFA.

TABLE 4

MEFA 13.1

| mefa aa# | 5' end site | epitope | hcv aa# | strain |
|---|---|---|---|---|
| 1–86 | NcoI | mutated hSOD (aa 70–72, ALA) | | |
| 89–106 | MluI | E1 | 303–320 | 1 |
| 109–129 | HindIII | E2 HVR1a consensus | 390–410 | 1 |
| 130–160 | | E2 HVR1 + 2 consensus | 384–414 | 1, 2 |
| 163–379 | | C33C short | 1211–1457 | 1 |
| 382–428 | HindIII | 5-1-1 PImut* | 1689–1735 | 1 |
| 431–477 | NruI | 5-1-1 PImut* | 1689–1735 | 3 |
| 480–526 | ClaI | 5-1-1 PImut* | 1689–1735 | 2 |
| 529–564 | AvaI | C100 | 1901–1936 | 1 |
| 567–602 | XbaI | NS5 | 2278–2313 | 1 |
| 605–640 | BglII | NS5 | 2278–2313 | 1 |
| 641–728 | | core | 9–53, R47L | 1 |
| | | epitopes | 64–88 | 1 |
| | | | 67–84 | 2 |
| 729–816 | | core | 9–53, R47L | 1 |
| | | epitopes | 64–88 | 1 |
| | | | 67–84 | 2 |

*The 5-1-1 epitopes are modified by eliminating possible cleavage sites (CS or CA) targeted by the NS3/4a recombinant protein. Instead of CS or CA, the sequence has been changed to PI. Additionally, the SOD protein is mutated so that the detection conjugate, an HRP-labeled anti-SOD antibody does not bind the MEFA. The core epitope is mutated to prevent the antibodies to HCV core, used in detection, from binding to the MEFA.

In one assay format, the sample is combined with the solid support, as described further below. If the sample is infected with HCV, core antigens, as well as HCV antibodies to those epitopes present on the solid support, will bind to the solid support components. A detectably labeled anti-core antibody is then added. The labeled anti-core antibody is directed against a different epitope than the anti-core antibody that is bound to the solid support. This anti-core antibody binds the core antigen captured by the anti-core antibodies on the solid support.

An antigen that reacts with the captured HCV antibody from the biological sample, which captured sample HCV antibody is reactive with the NS3/4a epitope, is also added. This antigen is preferably an epitope derived from the NS3 region of the HCV polyprotein. This antigen binds the captured HCV antibody from the sample. A number of antigens including such epitopes are known, including, but not limited to antigens derived from the c33c and c100 regions, as well as fusion proteins comprising an NS3 epitope, such as c25. These and other NS3 epitopes are useful in the present assays and are known in the art and described in, e.g., Houghton et al, U.S. Pat. No. 5,350,671; Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778; and commonly owned, allowed U.S. patent application Ser. Nos. 08/403,590 and 08/444,818, the disclosures of which are incorporated herein by reference in their entireties.

A second labeled antibody, directed against the antigen described above, is added. This antibody can be directed against any epitope included in the antigen. For example, the antibody can be directed against the NS3 region present in the antigen. Alternatively, if the antigen above is expressed as a fusion protein, the second labeled antibody can be directed against the fusion partner. Additional antigens and antibodies can be added to the assay, particularly if the solid support includes a MEFA. These assay formats are explained further below.

A representative assay under the invention is depicted in FIG. 2. As shown in the figure, the solid support includes two anti-core monoclonal antibodies, termed c11-3 and c11-7. These antibodies are directed against an epitope found in the N-terminal region of the core protein at amino acids 10–53, numbered relative to the HCV1 polyprotein sequence. The solid support also includes an epitope to NS3/4a. The biological sample is added to the solid support. HCV core antigen, as well as antibodies directed against the NS3/4a epitope, both present in the sample, will bind the capture reagents on the solid support.

Horse radish peroxidase (HRP)-labeled anti-core monoclonal antibody c11-14, directed against a C-terminal region of the core found at amino acid positions 120–130, numbered relative to the HCV1 polyprotein sequence, is then added. A fusion protein, comprising a sequence from human SOD (hSOD) and an epitope from the c33c region is added, as is a second HRP-labeled antibody, directed against the SOD portion of the fusion protein. The SOD-c33c fusion will bind to the anti-NS3 antibody and the anti-SOD antibody will, in turn, bind the SOD-c33c fusion protein. Detection of the label indicates the presence of HCV infection.

Figure 8:
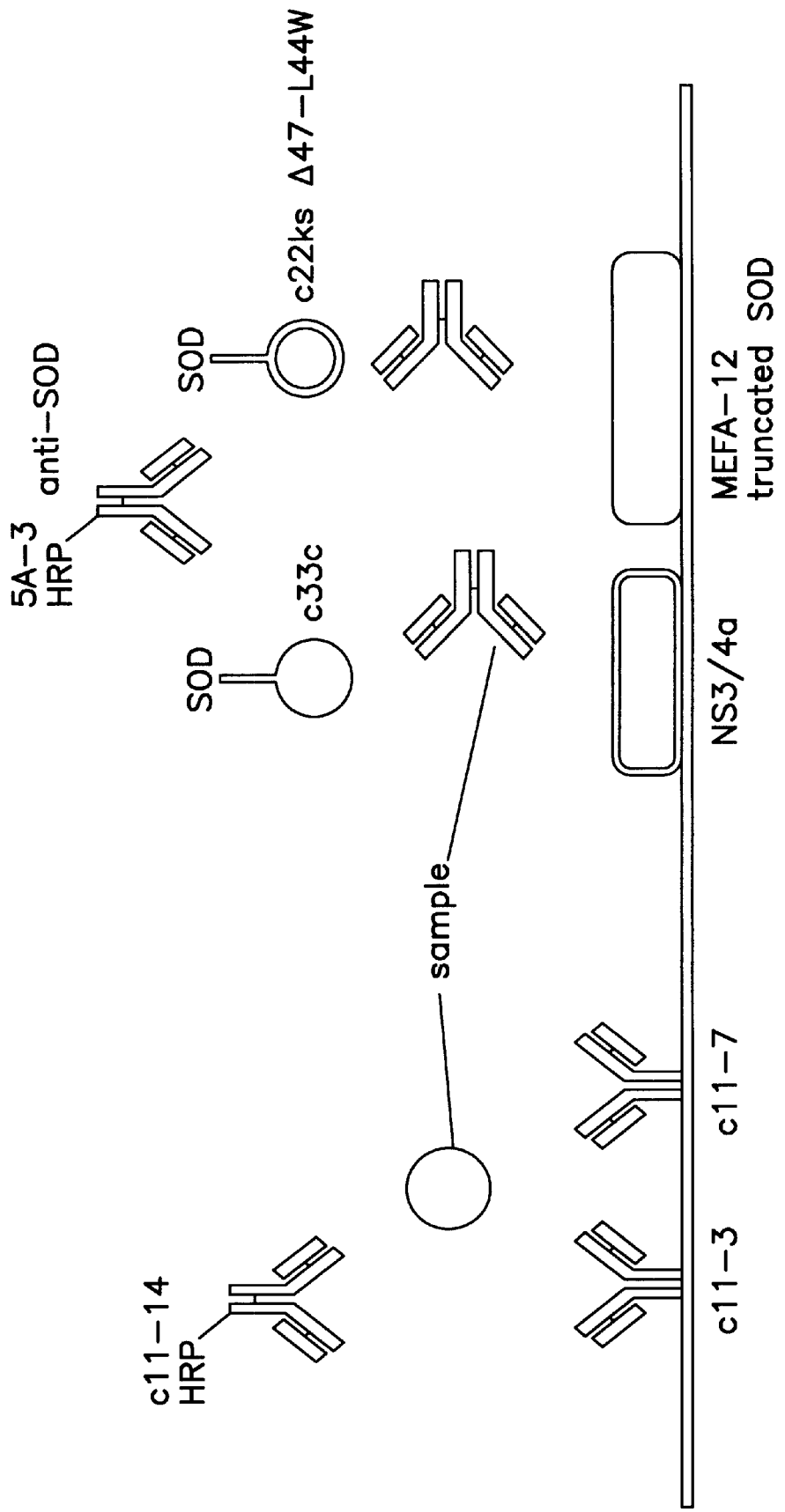
FIG. 8 is a schematic drawing of a representative immunoassay under the invention, using MEFA 12.

Another representative assay under the invention is depicted in FIG. 8. The antibody assay configuration is an antigen-antibody-antigen sandwich capture assay using both NS3/4a and MEFA 12. The solid support includes the two anti-core monoclonal antibodies described above, an epitope to NS3/4a, as well as a representative MEFA, MEFA 12, which includes a truncated version of human SOD. As with the assay above, the biological sample is added to the solid support. HCV core antigen, as well as antibodies directed against the NS3/4a epitope and epitopes of the MEFA, present in the sample, will bind the capture reagents on the solid support. Two antigens, one reactive with sample antibodies that bind NS3/4a (as described above) and one reactive with sample antibodies that bind MEFA 12, are added. In FIG. 8, the antigen reactive with the MEFA 12/sample antibody complex, is a fusion between an SOD molecule and c22ks Δ47-L44W. The c22ks antigen is from the core region and includes amino acids $Lys_{10}$ to $Ser_{99}$ of the polyprotein, as well as a deletion of Arg47 normally present and a substitution of Leu for Trp at position 44. The antibody detection conjugate is the second HRP-labeled monoclonal anti-SOD antibody, described above.

The above-described antigen/antibody combination assays are particularly advantageous as both the HCV core antigen and antibodies to NS3/4a and/or core may be detected by the same support in the same assay. Moreover, as described above, additional HCV epitopes, such as SOD-fused to c100, 5-1-1, NS5 antigens, as well as a protein resulting from a frameshift in the core region of the polyprotein, such as described in International Publication No. WO 99/63941, may be used in the combination cocktail to cover other non-structural epitopes of HCV.

In order to further an understanding of the invention, a more detailed discussion is provided below regarding production of antibodies for use in the subject immunoassays; production of polypeptides for use in the immunoassays; and methods of conducting the immunoassays.

Production of Antibodies for use in the HCV Immunoassays

As explained above, the assay utilizes various antibodies which are bound to a solid support (e.g., one or more anti-core antibodies), and that detect antigen/antibody complexes formed when HCV infection is present in the sample. These antibodies may be polyclonal or monoclonal antibody preparations, monospecific antisera, human antibodies, or may be hybrid or chimeric antibodies, such as humanized antibodies, altered antibodies, F(ab')$_2$ fragments, F(ab) fragments, Fv fragments, single-domain antibodies, dimeric or trimeric antibody fragment constructs, minibodies, or functional fragments thereof which bind to the antigen in question.

Antibodies are produced using techniques well known to those of skill in the art and disclosed in, for example, U.S. Pat. Nos. 4,011,308; 4,722,890; 4,016,043; 3,876,504; 3,770,380; and 4,372,745. For example, polyclonal antibodies are generated by immunizing a suitable animal, such as a mouse, rat, rabbit, sheep or goat, with an antigen of interest. In order to enhance immunogenicity, the antigen can be linked to a carrier prior to immunization. Such carriers are well known to those of ordinary skill in the art. Immunization is generally performed by mixing or emulsifying the antigen in saline, preferably in an adjuvant such as Freund's complete adjuvant, and injecting the mixture or emulsion parenterally (generally subcutaneously or intramuscularly). The animal is generally boosted 2–6 weeks later with one or more injections of the antigen in saline, preferably using Freund's incomplete adjuvant. Antibodies may also be generated by in vitro immunization, using methods known in the art. Polyclonal antiserum is then obtained from the immunized animal. See, e.g., Houghton et al., U.S. Pat. No. 5,350,671, for a description of the production of anti-HCV polyclonal antibodies.

Monoclonal antibodies are generally prepared using the method of Kohler and Milstein (1975) Nature 256:495–497, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice).

The production of various anti-HCV monoclonal antibodies has been described in, e.g., Houghton et al., U.S. Pat. No. 5,350,671; Chien et al., International Publication No. WO 93/00365; commonly owned, allowed U.S. patent application Ser. Nos. 08/403,590 and 08/444,818; and Kashiwakuma et al., U.S. Pat. No. 5,871,904, incorporated herein by reference in their entireties.

As explained above, antibody fragments which retain the ability to recognize the antigen of interest, will also find use in the subject immunoassays. A number of antibody fragments are known in the art which comprise antigen-binding sites capable of exhibiting immunological binding properties of an intact antibody molecule. For example, functional antibody fragments can be produced by cleaving a constant region, not responsible for antigen binding, from the antibody molecule, using e.g., pepsin, to produce F(ab')$_2$ fragments. These fragments will contain two antigen binding sites, but lack a portion of the constant region from each of the heavy chains. Similarly, if desired, Fab fragments, comprising a single antigen binding site, can be produced, e.g., by digestion of polyclonal or monoclonal antibodies with papain. Functional fragments, including only the variable regions of the heavy and light chains, can also be produced, using standard techniques such as recombinant production or preferential proteolytic cleavage of immunoglobulin molecules. These fragments are known as $F_v$. See, e.g., Inbar et al. (1972) *Proc. Nat. Acad. Sci. USA* 69:2659–2662; Hochman et al. (1976) *Biochem* 15:2706–2710; and Ehrlich et al. (1980) *Biochem* 19:4091–4096.

A single-chain Fv ("sFv" or "scFv") polypeptide is a covalently linked $V_H$-$V_L$ heterodimer which is expressed from a gene fusion including $V_H$- and $V_L$-encoding genes linked by a peptide-encoding linker. Huston et al. (1988) *Proc. Nat. Acad. Sci. USA* 85:5879–5883. A number of methods have been described to discern and develop chemical structures (linkers) for converting the naturally aggregated, but chemically separated, light and heavy polypeptide chains from an antibody V region into an sFv molecule which will fold into a three dimensional structure substantially similar to the structure of an antigen-binding site. See, e.g., U.S. Pat. Nos. 5,091,513, 5,132,405 and 4,946,778. The sFv molecules may be produced using methods described in the art. See, e.g., Huston et al. (1988) *Proc. Nat. Acad. Sci. USA* 85:5879–5883; U.S. Pat. Nos. 5,091,513, 5,132,405 and 4,946,778. Design criteria include determining the appropriate length to span the distance between the C-terminus of one chain and the N-terminus of the other, wherein the linker is generally formed from small hydrophilic amino acid residues that do not tend to coil or form secondary structures. Such methods have been described in the art. See, e.g., U.S. Pat. Nos. 5,091,513, 5,132,405 and 4,946,778. Suitable linkers generally comprise polypeptide chains of alternating sets of glycine and serine residues, and may include glutamic acid and lysine residues inserted to enhance solubility.

"Mini-antibodies" or "minibodies" will also find use with the present invention. Minibodies are sFv polypeptide chains which include oligomerization domains at their C-termini, separated from the sFv by a hinge region. Pack et al. (1992) *Biochem* 31:1579–1584. The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992) *Biochem* 31:1579–1584; Cumber et al. (1992) *J Immunology* 149B: 120–126.

Production of Antigens for use in the HCV Immunoassays

As explained above, the molecules of the present invention are generally produced recombinantly. Thus, polynucleotides encoding HCV antigens for use with the present invention can be made using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from viral nucleic acid molecules, using techniques described in the art, such as in Houghton et al., U.S. Pat. No. 5,350,671. The gene of interest can also be produced synthetically, rather than cloned. The molecules can be designed with appropriate codons for the particular sequence. The complete sequence is then assembled from overlapping oligonucleotides prepared by standard methods and assembled into a complete coding sequence. See, e.g., Edge (1981) *Nature* 292:756; Nambair et al. (1984) *Science* 223:1299; and Jay et al. (1984) *J. Biol. Chem.* 259:6311.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PVR. See, e.g., Jayaraman et al. (1991) *Proc. Natl. Acad. Sci. USA* 88:4084–4088. Additionally, oligonucleotide directed synthesis (Jones et al. (1986) *Nature* 54:75–82), oligonucleotide directed mutagenesis of pre-existing nucleotide regions (Riechmann et al. (1988) *Nature* 332:323–327 and Verhoeyen et al. (1988) *Science* 239:1534–1536), and enzymatic filling-in of gapped oligonucleotides using $T_4$ DNA polymerase (Queen et al. (1989) *Proc. Natl. Acad. Sci. USA* 86:10029–10033) can be used under the invention to provide molecules having altered or enhanced antigen-binding capabilities, and/or reduced immunogenicity.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements.

The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence which can later be removed by the host in post-translational processing. See, e.g., U.S. Pat. Nos. 4,431,739; 4,425,437; 4,338,397.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer (Dijkema et al. (1985) *EMBO J.* 4:761), the enhancer/promoter derived from the long terminal repeat (LTR) of the Rous Sarcoma Virus (Gorman et al. (1982) *Proc. Natl. Acad. Sci. USA* 79:6777) and elements derived from human CMV (Boshart et al. (1985) *Cell* 41:521), such as elements included in the CMV intron A sequence (U.S. Pat. No. 5,688,688). The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

As explained above, it may also be desirable to produce mutants or analogs of the antigen of interest. This is particularly true with NS3/4a. Methods for doing so are described in, e.g., Dasmahapatra et al., U.S. Pat. No. 5,843,752 and Zhang et al., U.S. Pat. No. 5,990,276. Mutants or analogs of this and other HCV proteins for use in the subject assays may be prepared by the deletion of a portion of the sequence encoding the polypeptide of interest, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; Kunkel, T. A. (1985) *Proc. Natl. Acad. Sci. USA* (1985) 82:448; Geisselsoder et al. (1987) *BioTechniques* 5:786; Zoller and Smith (1983) *Methods Enzymol.* 100:468; Dalbie-McFarland et al. (1982) *Proc. Natl. Acad. Sci USA* 79:6409.

The molecules can be expressed in a wide variety of systems, including insect, mammalian, bacterial, viral and yeast expression systems, all well known in the art.

For example, insect cell expression systems, such as baculovirus systems, are known to those of skill in the art and described in, e.g., Summers and Smith, *Texas Agricultural Experiment Station Bulletin* No. 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtilis*, and Streptococcus spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Nucleic acid molecules comprising nucleotide sequences of interest can be stably integrated into a host cell genome or maintained on a stable episomal element in a suitable host cell using various gene delivery techniques well known in the art. See, e.g., U.S. Pat. No. 5,399,346.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

The recombinant production of various HCV antigens has been described. See, e.g., Houghton et al., U.S. Pat. No. 5,350,671; Chien et al., *J. Gastroent. Hepatol.* (1993) 8:S33–39; Chien et al., International Publication No. WO 93/00365; Chien, D. Y., International Publication No. WO 94/01778.

Immunodiagnostic Assays

Once produced, the above anti-core antibodies and NS3/4a antigens are placed on an appropriate solid support for use in the subject immunoassays. A solid support, for the purposes of this invention, can be any material that is an insoluble matrix and can have a rigid or semi-rigid surface. Exemplary solid supports include, but are not limited to, substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. Particular supports include plates, pellets, disks, capillaries, hollow fibers, needles, pins, solid fibers, cellulose beads, pore-glass beads, silica gels, polystyrene beads optionally cross-linked with divinylbenzene, grafted co-poly beads, polyacrylamide beads, latex beads, dimethylacrylamide beads optionally crosslinked with N-N'-bis-acryloylethylenediamine, and glass particles coated with a hydrophobic polymer.

If desired, the molecules to be added to the solid support can readily be functionalized to create styrene or acrylate moieties, thus enabling the incorporation of the molecules into polystyrene, polyacrylate or other polymers such as polyimide, polyacrylamide, polyethylene, polyvinyl, polydiacetylene, polyphenylene-vinylene, polypeptide, polysaccharide, polysulfone, polypyrrole, polyimidazole, polythiophene, polyether, epoxies, silica glass, silica gel, siloxane, polyphosphate, hydrogel, agarose, cellulose, and the like.

In one context, a solid support is first reacted with the HCV anti-core antibodies and NS3/4a epitope (collectively called "the solid-phase components" herein), and optionally, one or more MEFAs, under suitable binding conditions such that the molecules are sufficiently immobilized to the support. Sometimes, immobilization to the support can be enhanced by first coupling the antigen and/or antibody to a protein with better solid phase-binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other reagents that can be used to bind molecules to the support include polysaccharides, polylactic acids, polyglycolic acids, polymeric amino acids, amino acid copolymers, and the like. Such molecules and methods of coupling these molecules to antigens, are well known to those of ordinary skill in the art. See, e.g., Brinkley, M. A. (1992) *Bioconjugate Chem.* 3:2–13; Hashida et al. (1984) *J. Appl. Biochem.* 6:56–63; and Anjaneyulu and Staros (1987) *International J. of Peptide and Protein Res.* 30:117–124.

After reacting the solid support with the solid-phase components, any nonimmobilized solid-phase components are removed from the support by washing, and the support-bound components are then contacted with a biological sample suspected of containing HCV antibodies and antigens (collectively called "ligand molecules" herein) under suitable binding conditions. After washing to remove any nonbound ligand molecules, a second anti-core antibody, directed against a different epitope than the anti-core antibody bound to the support, is added under suitable binding conditions. The added anti-core antibody includes a detectable label, as described above, and acts to bind any core antigen that might be present in the sample which has reacted with the support-bound anti-core antibody. Also added are one or more antigens that can react with antibodies present in the sample that have, in turn, reacted with the NS3/4A epitope. As explained above, the antigen is typically derived from the NS3 region of the HCV polyprotein, and particularly from the c33c region of HCV. See, Houghton et al., U.S. Pat. No. 5,350,671; Chien et al., *Proc. Natl. Acad. Sci.* (1989) 89:10011–10015; International Publication No. WO 93/00365; and commonly owned, allowed U.S. patent application Ser. Nos. 08/403,590 and 08/444,818, for a description of this region and epitopes derived therefrom. A labeled antibody directed against this antigen is also added. The antibody will therefore bind the antigen, which has reacted with anti-NS3 antibodies present in the sample. For this purpose, the c33c epitope can be conveniently provided as a fusion between c33c and human superoxide dismutase (hSOD), produced recombinantly e.g., by methods described in Houghton et al., U.S. Pat. No. 5,350,671. The nucleotide and amino acid sequences for human SOD are known and reported in Hallewell et al., U.S. Pat. No. 5,710,033. A labeled antibody directed against human SOD can therefore be used to detect the presence of complexes formed between the NS3/4a epitope, any antibodies in the sample which react with this epitope, and HCV polypeptides which in turn bind the antibody in the sample.

If a MEFA is present on the solid support, one or more additional antigens, reactive with antibodies from the biological sample which are bound to antigens present on the MEFA, may also be added to the assay. Particularly useful in this context is an antigen derived from the core region of HCV, and more particularly, from the c22 antigen which includes 119 N-terminal core amino acids of the HCV polyprotein. One particular antigen derived from c22 is c22ks Δ47-L44W which includes amino acids $Lys_{10}$ to $Ser_{99}$ of the polyprotein, as well as a deletion of Arg47 normally present and a substitution of Leu for Trp at position 44. As with the c33c epitope described above, this antigen can be provided as a fusion with hSOD and the same labeled antibody, directed against human SOD, can be used to detect the presence of complexes formed between antibodies present in the sample and the NS3/4a epitope and/or the MEFA, which complexes are also bound with the HCV antigens (e.g., c33c and c22).

More particularly, an ELISA method can be used, wherein the wells of a microtiter plate are coated with the solid-phase components. A biological sample containing or suspected of containing ligand molecules is then added to the coated wells. After a period of incubation sufficient to allow ligand-molecule binding to the immobilized solid-phase component, the plate(s) can be washed to remove unbound moieties and a detectably labeled secondary binding molecule (labeled anti-core antibody), an NS3 epitope-containing molecule, and an antibody directed against the NS3 epitope-containing molecule added. These molecules are allowed to react with any captured sample antigen and antibody, the plate washed and the presence of the labeled antibodies detected using methods well known in the art.

The above-described assay reagents, including the immunoassay solid support with bound antibodies and antigens, as well as antibodies and antigens to be reacted with the captured sample, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

HCV Antigen/Antibody Combination Immunoassay

The present HCV antigen/antibody combination immunoassay was compared to other HCV assays to test the seroconversion detection limits and compare these limits to those obtained in other commercially available assays as follows.

A. Materials and Methods

Blood Samples: Panels of commercially available human blood samples were used. Such panels are available from, e.g., Boston Biomedica, Inc., West Bridgewater, Mass. (BBI); Bioclinical Partners, Franklin, Mass. (BCP); and North American Biologics, Inc., BocoRatan, Fla. (NABI). The days indicated in Tables 5 and 6 are days on which blood was collected from the subjects.

Monoclonal Antibodies: Monoclonal antibodies c11-3, c 1-7 and c 1-14 were obtained from Ortho Clinical Diagnostics, Raritan, N.J. The c11-3 and c11-7 antibodies are directed against an N-terminal portion of the core (amino acids 10–53, numbered relative to the HCV1 polyprotein). Monoclonal antibody c11-14 is directed against a C-terminal portion of the core (amino acids 120–130, numbered relative to the HCV1 polyprotein). The c11-14 antibody was conjugated to horse radish peroxidase (HRP) using standard procedures.

Monoclonal antibody 5A-3 is an anti-SOD antibody directed against amino acids 1 to 65 of SOD and was made using standard techniques. The antibody was conjugated to HRP as described above.

B. Antigens:

The c33c antigen (266 amino acids, amino acids 1192 to 1457 of the HCV1 polyprotein) was expressed as an internal SOD fusion polypeptide in E. coli by methods described for the synthesis of the 5-1-1 antigen (Choo, et al., Science (1989) 244:359–362, herein incorporated by reference). The recombinant antigen was purified as described in Chien, et al., Proc. Natl. Acad. Sci. (1989) 89:10011–10015 (herein incorporated by reference). See, also, Houghton et al., U.S. Pat. No. 5,350,671, for production protocols for SOD-c33c.

The NS3/4a epitope used in the assay is a conformational epitope having the sequence specified in FIG. 3.

C. Immunoassay Formats:

The Abbott PRISM assay (Abbott Laboratories, Abbott Park, Ill.), is commercially available and is an antibody-based detection assay. The assay was performed using the manufacturer's instructions.

The ORTHO HCV Version 3.0 ELISA Test System (termed Ortho 3.0 assay herein, Ortho Clinical Diagnostics, Raritan, N.J.) is an antibody-based detection assay. The assay was conducted using the manufacturer's instructions.

The Roche Amplicor assay (Roche, Pleasant, Calif.) is a commercially available PCR-based assay. The assay was performed using the manufacturer's instructions.

The Gen-Probe TMA assay (San Diego, Calif.) is a commercially available transcription-mediated amplification assay. The assay was performed using the manufacturer's instructions.

The Ortho antigen assay (Ortho Clinical Diagnostics, Raritan, N.J.) is an antigen-based detection assay. The assay was performed using the manufacturer's instructions.

The subject HCV antigen/antibody combination immunoassay was performed as follows. 4mg/mL each of purified monoclonal antibodies C11-7 and C11-3 in 1× phosphate-buffered saline (PBS), pH 7.4 were combined and mixed well. 90 ng of the NS3/4a recombinant antigen was added to the same coating buffer. The solution was mixed for 30 minutes prior to coating. 200 mL of the above solution was added per well to 96-well Costar medium binding microtiter plates (Corning, Inc.) Plates were incubated at 15–30° C. for 16–24 hours. Plates were washed two times with $dH_2O$, followed with 300 µL/well postcoat buffer (1% bovine serum albumin (BSA), 1×PBS) for 1 hour and 300 µl/well stability buffer (1×PBS, 1% BSA, mannitol, polyethylene glycol (PEG), gelatin) for 1 hour. Plates were aspirated and dried at 4° C. in a lyophilizer for 24 hours. Plates were pouched with desiccant.

To conduct the antigen/antibody combination immunoassay, 100 µL of enhanced lysis buffer (1% N-laurylsarcosine, 0.65M NaCl, 50 mg/mL mouse IgG technical grade (Sigma, St. Louis, Mo.), 1% BSA sulfhydryl-modified (Bayer), 0.1% Casein) were added to the plate. 100 mL of sample were then added. This was incubated on a shaker at 40° C. for one hour. The plates were washed six times with 1×PBS, 0.1% Tween-20, on an Ortho Plate Washer. 200 mL conjugate solution (1:75 dilution c11-14-HRP with 250 ng/assay SOD-c33c antigen plus 1:5000 dilution mouse anti-SOD-HRP in HCV 3.0 sample diluent (from ORTHO HCV Version 3.0 ELISA Test System, Ortho Clinical Diagnostics, Raritan, N.J.) without SOD extract, all prepared 30 minutes prior to addition). The solution was incubated 45 minutes with shaking at 40° C. This was washed six times, as above, and 200 mL substrate solution (1 OPD tablet/10 mL) was added. The OPD tablet contains o-phenylenediamine dihydrochloride and hydrogen peroxide for horse radish peroxidase reaction color development and is available from Sigma, St. Louis, Mo. This was incubated 30 minutes at 15–30° C. in the dark. The reaction was stopped by addition of 50 mL 4N $H_2SO_4$ and the plates were read at 492 nm, relative to absorbance at 690 nm as control.

D. Results:

The results of the various assays are shown in Tables 5 and 6, which depict two separate experiments done on blood samples exposed to HCV infection as indicated. Shaded areas indicate detection of virus. As shown in below, Chiron's combination antigen/antibody assay detected seroconversion in all samples, while all other antibody- and antigen-based assays failed to detect seroconversion in at least one sample. In particular, neither of the antibody-based assays detected seroconversion until at least day 18 (Table 5). Table 6 shows that neither of the antibody-based assays detected the presence of HCV infection at day 22. Moreover, the Ortho antigen-based assay failed to detect seroconversion from days 85 on.

Thus, based on the above results, it is clear that the novel combination antibody/antigen assay reduces the number of false negatives obtained using other conventional antibody- and antigen-based assays.

TABLE 5

HCV Seroconversion

| Days | Abbott PRISM | Ortho 3.0 | Roche Amplicor | Gen-Probe TMA | Ortho Ag | Chiron Ag/Ab |
|---|---|---|---|---|---|---|
| 0 | 0.1 | 0.0 | >5 × 10^5 | 9.25 | 18.6 | 2.8 |
| 4 | 0.1 | 0.0 | >5 × 10^5 | 9.29 | 19.0 | 3.1 |
| 7 | 0.1 | 0.0 | >5 × 10^5 | 9.52 | 22.3 | 1.5 |
| 13 | 0.3 | 0.1 | >5 × 10^5 | 9.59 | 26.2 | 1.7 |
| 18 | 1.3 | 0.4 | >5 × 10^5 | 9.70 | 15.9 | 1.2 |
| 21 | 1.1 | 1.0 | >5 × 10^5 | 9.39 | 11.1 | 1.5 |
| 164 | 4.2 | 4.4 | 4 × 10^5 | 9.28 | 0.11 | 2.5 |

TABLE 6

HCV Seroconversion

| Days | Abbott PRISM | Ortho 3.0 | Roche Amplicor | Gen-Probe TMA | Ortho Ag | Chiron Ag/Ab |
|---|---|---|---|---|---|---|
| 0 | 0.1 | 0.0 | BLD | | 0.11 | 0.5 |
| 13 | 0.1 | 0.0 | >5 × 10^5 | | 44.0 | 3.0 |
| 20 | 0.1 | 0.0 | >5 × 10^5 | | 24.2 | 1.3 |
| 22 | 0.3 | 0.0 | >5 × 10^5 | | 29.2 | 1.6 |
| 85 | 5.4 | 4.7 | BQR | | 0.06 | 1.1 |
| 131 | 4.3 | 4.7 | BQR | | 0.09 | 1.0 |
| 135 | 4.6 | 4.7 | 3 × 10^5 | | 0.09 | 1.2 |
| 138 | 5.5 | 4.7 | BLD | | 0.08 | 1.2 |
| 146 | 5.9 | 4.7 | BLD | | 0.11 | 2.1 |
| 152 | 5.4 | 4.7 | BQR | | 0.07 | 1.8 |

EXAMPLE 2

Production of an NS3/4a Conformational Epitope with Thr to Pro and Ser to Ile Substitutions A conformational epitope of NS3/4a was obtained as follows. This epitope has the sequence specified in FIGS. 4A through 4D and differs from the native sequence at positions 403 (amino acid 1428 of the HCV-1 full-length sequence) and 404 (amino acid 1429 of the HCV-1 full-length sequence). Specifically, the Thr normally occurring at position 1428 of the native sequence has been mutated to Pro and Ser which occurs at position 1429 of the native sequence has been mutated to Ile.

In particular, the yeast expression vector used was pBS24.1, described above. Plasmid pd.hcv1a.ns3ns4aPI, which encoded a representative NS3/4a epitope used in the subject immunoassays, was produced as follows. A two step procedure was used. First, the following DNA pieces were ligated together: (a) synthetic oligonucleotides which would provide a 5' HindIII cloning site, followed by the sequence ACAAAACAAA, the initiator ATG, and codons for HCV1a, beginning with amino acid 1027 and continuing to a BglI site at amino acid 1046; (b) a 683 bp BglI-ClaI restriction fragment (encoding amino acids 1046–1274) from pAcHLTns3ns4aPI; and (c) a pSP72 vector (Promega, Madison, Wis., GenBank/EMBL Accession Number X65332) which had been digested with HindIII and ClaI, dephosphorylated, and gel-purified. Plasmid pAcHLTns3ns4aPI was derived from pAcHLT, a baculovirus expression vector commercially available from BD Pharmingen (San Diego, Calif.). In particular, a pAcHLT EcoRI-PstI vector was prepared, as well as the following fragments: EcoRI-AlwnI, 935 bp, corresponding to amino acids 1027–1336 of the HCV-1 genome; AlwnI-SacII, 247 bp, corresponding to amino acids 1336–1419 of the HCV-1 genome; HinfI-BglI, 175 bp, corresponding to amino acids 1449–1509 of the HCV-1 genome; BglI-PstI, 619 bp, corresponding to amino acids 1510–1711 of the HCV-1 genome, plus the transcription termination codon. A SacII-HinfI synthetically generated fragment of 91 bp, corresponding to amino acids 1420–1448 of the HCV-1 genome and containing the PI mutations (Thr-1428 mutated to Pro, Ser-1429 mutated to Ile), was ligated with the 175 bp HinfI-BglI fragment and the 619 bp BglI-PstI fragment described above and subcloned into a pGEM-5Zf(+) vector digested with SacII and PstI. pGEM-5Zf(+) is a commercially available *E. coli* vector (Promega, Madison, Wis., GenBank/EMBL Accession Number X65308). After transformation of competent HB101 cells, miniscreen analysis of individual clones and sequence verification, an 885 bp SacII-PstI fragment from pGEM5.PI clone2 was gel-purified. This fragment was ligated with the EcoRI-AlwnI 935 bp fragment, the AlwnI-SacII 247 bp fragment and the pAcHLT EcoRI-PstI vector, described above. The resultant construct was named pAcHLTns3ns4aPI.

The ligation mixture above was transformed into HB101-competent cells and plated on Luria agar plates containing 100 μg/ml ampicillin. Miniprep analyses of individual clones led to the identification of putative positives, two of which were amplified. The plasmid DNA for pSP72 1aHC, clones #1 and #2 were prepared with a Qiagen Maxiprep kit and were sequenced.

Figure 5:
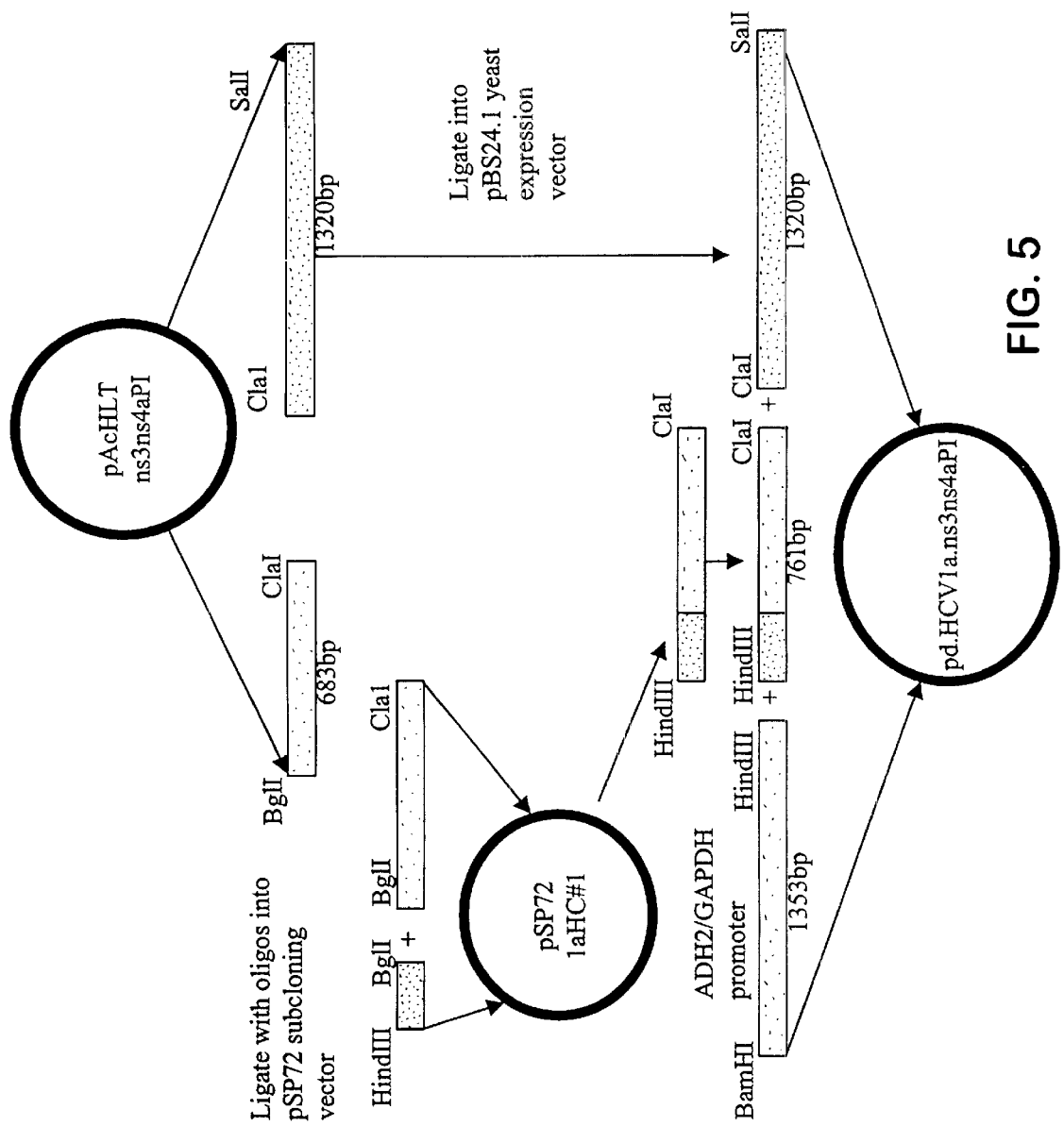
FIG. 5 is a diagram of the construction of pd.HCV1a.ns3ns4aPI.

Next, the following fragments were ligated together: (a) a 761 bp HindIII-ClaI fragment from pSP721aHC #1 (pSP72.1aHC was generated by ligating together the following: pSP72 which had been digested with HindIII and ClaI, synthetic oligonucleotides which would provide a 5' HindIII cloning site, followed by the sequence ACAAAA-CAAA (SEQ ID NO:7), the initiation codon ATG, and codons for HCV1a, beginning with amino acid 1027 and continuing to a BglII site at amino acid 1046, and a 683 bp BglII-ClaI restriction fragment (encoding amino acids 1046–1274) from pAcHLTns3ns4aPI); (b) a 1353 bp BamHI-HindIII fragment for the yeast hybrid promoter ADH2/GAPDH; (c) a 1320 bp ClaI-SalI fragment (encoding HCV1a amino acids 1046–1711 with Thr 1428 mutated to Pro and Ser 1429 mutated to Ile) from pAcHLTns3ns4aPI; and (d) the pBS24.1 yeast expression vector which had been digested with BamHI and SalI, dephosphorylated and gel-purified. The ligation mixture was transformed into competent HB 101 and plated on Luria agar plates containing 100 μg/ml ampicillin. Miniprep analyses of individual colonies led to the identification of clones with the expected 3446 bp BamHI-SalI insert which was comprised of the ADH2/GAPDH promoter, the initiator codon ATG and HCV1a NS3/4a from amino acids 1027–1711 (shown as amino acids 1–686 of FIGS. 4A–4D), with Thr 1428 (amino acid position 403 of FIGS. 4A–4D) mutated to Pro and Ser 1429 (amino acid position 404 of FIGS. 4A–4D) mutated to Ile. The construct was named pd.HCV1a.ns3ns4aPI (see, FIG. 5).

*S. cerevisiae* strain AD3 was transformed with pd.HCV1a.ns3ns4aPI and single transformants were checked for expression after depletion of glucose in the medium. The recombinant protein was expressed at high levels in yeast, as detected by Coomassie blue staining and confirmed by immunoblot analysis using a polyclonal antibody to the helicase domain of NS3.

EXAMPLE 3

Purification of NS3/4a Conformational Epitope

The NS3/4a conformational epitope was purified as follows. *S. cerevisiae* cells from above, expressing the NS3/4a epitope were harvested as described above. The cells were suspended in lysis buffer (50 mM Tris pH 8.0, 150 mM NaCl, 1 mM EDTA, 1 mM PMSF, 0.1 μM pepstatin, 1 μM leupeptin) and lysed in a Dyno-Mill (Wab Willy A. Bachofon, Basel, Switzerland) or equivalent apparatus using glass beads, at a ratio of 1:1:1 cells:buffer:0.5 mm glass-beads. The lysatewas centrifuged at 30100×g for 30 min at 4° C. and the pellet containing the insoluble protein fraction was added to wash buffer (6 ml/g start cell pellet weight) and rocked at room temperature for 15 min. The wash buffer consisted of 50 mM NaPO$_4$ pH 8.0, 0.3 M NaCl, 5 mM β-mercaptoethanol, 10% glycerol, 0.05% octyl glucoside, 1 mM EDTA, 1 mM PMSF, 0.1 μM pepstatin, 1 μM leupeptin. Cell debris was removed by centrifugation at 30100×g for 30 min at 4° C. The supernatant was discarded and the pellet retained.

Protein was extracted from the pellet as follows. 6 ml/g extraction buffer was added and rocked at room temperature for 15 min. The extraction buffer consisted of 50 mM Tris pH 8.0, 1 M NaCl, 5 mM β-mercaptoethanol, 10% glycerol, 1 mM EDTA, 1 mM PMSF, 0.1 μM pepstatin, 1 μM leupeptin. This was centrifuged at 30100×g for 30 min at 4° C. The supernatant was retained and ammonium sulfate added to 17.5% using the following formula: volume of supernatant (ml) multiplied by x % ammonium sulfate/(1−x % ammonium sulfate)=ml of 4.1 M saturated ammonium sulfate to add to the supernatant. The ammonium sulfate was added dropwise while stirring on ice and the solution stirred on ice for 10 min. The solution was centrifuged at 17700×g for 30 min at 4° C. and the pellet retained and stored at 2° C. to 8° C. for up to 48 hrs.

The pellet was resuspended and run on a Poly U column (Poly U Sepharose 4B, Amersham Pharmacia) at 4° C. as follows. Pellet was resuspended in 6 ml Poly U equilibration buffer per gram of pellet weight. The equilibration buffer consisted of 25 mM HEPES pH 8.0, 200 mM NaCl, 5 mM DTT (added fresh), 10% glycerol, 1.2 octyl glucoside. The solution was rocked at 4° C. for 15 min and centrifuged at 31000×g for 30 min at 4° C.

A Poly U column (1 ml resin per gram start pellet weight) was prepared. Linear flow rate was 60 cm/hr and packing flow rate was 133% of 60 cm/hr. The column was equilibrated with equilibration buffer and the supernatant of the resuspended ammonium sulfate pellet was loaded onto the equilibrated column. The column was washed to baseline with the equilibration buffer and protein eluted with a step elution in the following Poly U elution buffer: 25 mM HEPES pH 8.0, 1 M NaCl, 5 mM DTT (added fresh), 10% glycerol, 1.2 octyl glucoside. Column eluate was run on SDS-PAGE (Coomassie stained) and aliquots frozen and stored at −80° C. The presence of the NS3/4a epitope was confirmed by Western blot, using a polyclonal antibody directed against the NS3 protease domain and a monoclonal antibody against the 5-1-1 epitope (HCV 4a).

Additionally, protease enzyme activity was monitored during purification as follows. An NS4A peptide (KKGSVVIVGRIVLSGKPAIIPKK (SEQ ID NO:8)), and the sample containing the NS3/4a conformational epitope, were diluted in 90 μl of reaction buffer (25 mM Tris, pH 7.5, 0.15M NaCl, 0.5 mM EDTA, 10% glycerol, 0.05 n-Dodecyl B-D-Maltoside, 5 mM DTT) and allowed to mix for 30 minutes at room temperature. 90 μl of the mixture were added to a microtiter plate (Costar, Inc., Corning, N.Y.) and 10 μl of HCV substrate (AnaSpec, Inc., San Jose Calif.) was added. The plate was mixed and read on a Fluostar plate reader. Results were expressed as relative fluorescence units (RFU) per minute.

Using these methods, the product of the 1 M NaCl extraction contained 3.7 RFU/min activity, the ammonium sulfate precipitate had an activity of 7.5 RFU/min and the product of the Poly U purification had an activity of 18.5 RFU/min.

EXAMPLE 4

Competition Studies

The following competition study was conducted in order to assess whether the NS3/4a conformational epitope detected different antibodies than other HCV antigens. In particular, the NS3/4a antigen was compared with the c200 antigen as follows.

0.5 μg and 1.0 μg of NS3/4a, produced as described above, or c200 (*Hepatology* (1992) 15:19–25, available in the ORTHO HCV Version 3.0 ELISA Test System, Ortho-Clinical Diagnostics, Raritan, N.J.), were mixed with 20 μl of sample PHV914-5 (an early seroconversion bleed obtained from blood of an infected individual) in a total volume of 220 μl (1×PBS). The mixture was incubated for 1 hour in microwells at 37° C. The mixture was then transferred to NS3/4a-coated plates and incubated for 1 hour at 37° C. Plates were washed and assayed as follows.

1 μg of c200 antigen was added to 10 μl of sample PHV914-5 in a total volume of about 220 μl. The mixture was incubated for 1 hour in a micro well at 37° C. and 200 μl transferred to an NS3/4a-coated plate (100 ng/assay) and incubated for 1 hour at 37° C. Plates were washed five times with 1×PBS, 0.1% Tween-20. 200 μl of conjugate solution (described above) were added, and the plates incubated and assayed. Controls which consisted of PHV914-5 and 1×PBS (without antigen) were also treated as above.

Results are shown in Table 7. Percent inhibition results shown in column 4 are calculated as column 3 minus (column 2 divided by column 3 times 100). As can be seen, the data show that NS34a is neutralized by early seroconversion antibodies and c200 is not. A strong signal was achieved when antibodies in PHV914-5 c33c early seroconversion panel member reacted with the NS34a coated on the plate. The c200 antigen was not neutralized by these antibodies. This is shown in the top panel of Table 7. When NS34a was mixed with the PHV914-5 sample, it was neutralized and therefore no antibodies were present in the sample to react with NS34a that was coated on the microplate. The data indicate that NS34a may be detecting a different class of antibodies than is detected by c200.

TABLE 7

Competition Studies to Show NS34a Antigen Detects Different Antibodies in Early c33c Seroconversion Panel Compared to c200 Antigen

| c200 | 1 | 2<br>PHV914-5<br>s | 3<br>*Control 1xPBS<br>s | 4<br>% Inhibition |
|---|---|---|---|---|
| 1 ug |  | 1.450 | 1.645 | 12 |
| 1 ug |  | 1.545 | 1.687 | 8 |
| 0.5 ug |  | 1.557 | 1.913 | 19 |
| 0.5 ug |  | 1.719 | 1.804 | 5 |
| NS3/4a | + | PHV914-5<br>s | s |  |
| 1 ug |  | 0.054 | 1.599 | 97 |
| 1 ug |  | 0.037 | 1.677 | 98 |
| 0.5 ug |  | 0.066 | 1.672 | 96 |
| 0.5 ug |  | NA | 1.524 | NA |

EXAMPLE 5

Stability Studies of NS3/4a Conformational Epitope

To assess the role of stability of the NS3/4a epitope to assay performance, the following study was done to determine NS3/4a immunoreactivity versus time at room temperature. Small aliquots of stock NS3/4a were allowed to sit at room temperature and then frozen at intervals as shown in Table 8. All vials were coated simultaneously and tested against two early NS3 seroconversion panels.

As can be seen in Table 8, the NS3/4a stock is not stable and immunoreactivity decreases with time. In addition, maintaining NS3/4a conformation is necessary for immunoreactivity.

Further stability studies were conducted as follows. Two conformational monoclonal antibodies made against NS3/4a using standard procedures were substituted for anti-HCV early seroconversion panels. Stock NS3/4a vials were stored at room temperature at time intervals 3, 6 and 24 hours. The NS3/4a from the frozen vials was coated at 90 ng/ml and assayed using the procedure described above. Results suggested that the two monoclonals were indeed conformational and their reactivity was sensitive to the handling of stock NS3/4a antigen at room temperature. The reactivity of a positive control monoclonal antibody did not change.

TABLE 8

| Time (hrs) | 0 | 6 | 21.4 | 29 | 35.5 | 46 | 52 | control |
|---|---|---|---|---|---|---|---|---|
|  | A | D | G | H | I | K | N | Reference |
|  | s/co | s/co | s/co | s/co | s/co | s/co | s/co | s/co |
| PHV 904-1 | 0.0 | 0.0 | 0.0 | 0.0 | 0.0 | 0.0 | 0.0 | 0.0 |
| PHV 904-2 | 0.0 | 0.0 | 0.0 | 0.0 | 0.0 | 0.0 | 0.0 | 0.0 |
| PHV 904-3 | 1.5 | 0.3 | 0.1 | 0.0 | 0.0 | 0.0 | 0.0 | 1.8 |
| PHV 904-4 | 3.7 | 1.0 | 0.2 | 0.1 | 0.1 | 0.1 | 0.1 | 4.4 |
| PHV 904-5 | 4.8 | 2.0 | 0.7 | 0.6 | 0.3 | 0.2 | 0.3 | 5.5 |
| PHV 904-6 | 5.4 | 2.8 | 1.1 | 1.0 | 0.6 | 0.5 | 0.6 | 5.8 |
| PHV 904-7 | 5.1 | 3.4 | 1.5 | 1.0 | 1.1 | 0.5 | 0.7 | 5.4 |
| PHV 914-1 | 0.0 | 0.0 | 0.0 | 0.0 | 0.0 | 0.0 | 0.0 | 0.0 |
| PHV 914-2 | 0.0 | 0.0 | 0.0 | 0.0 | 0.0 | 0.0 | 0.0 | 0.0 |
| PHV 914-3 | 0.0 | 0.0 | 0.0 | 0.0 | 0.0 | 0.0 | 0.0 | 0.0 |
| PHV 914-4 | 0.5 | 0.1 | 0.0 | 0.0 | 0.0 | 0.0 | 0.0 | 0.7 |
| PHV 914-5 | 2.1 | 0.4 | 0.0 | 0.0 | 0.0 | 0.0 | 0.0 | 3.0 |
| PHV 914-6 | 2.5 | 0.4 | 0.0 | 0.0 | 0.0 | 0.0 | 0.0 | 3.4 |
| PHV 914-7 | 2.8 | 0.5 | 0.1 | 0.1 | 0.0 | 0.0 | 0.0 | 4.9 |
| PHV 914-8 | 2.9 | 0.7 | 0.1 | 0.1 | 0.1 | 0.1 | 0.1 | 4.9 |
| Enzyme |  |  |  |  |  |  |  |  |
| RFU/min | 8.75 | 4.14 | 3.08 | 1.88 | 1.75 | 1.75 | 0.75 |  |

EXAMPLE 6

Immunoreactivity of NS3/4a Conformational Epitope Verus Denatured NS3/4a

The immunoreactivity of the NS3/4a conformational epitope, produced as described above, was compared to NS3/4a which had been denatured by adding SDS to the NS3/4a conformational epitope preparation to a final concentration of 2%. The denatured NS3/4a and conformational NS3/4a were coated onto microtiter plates as described above. The c200 antigen (*Hepatology* (1992) 15:19–25, available in the ORTHO HCV Version 3.0 ELISA Test System, Ortho-Clinical Diagnostics, Raritan, N.J.) was also coated onto microtiter plates. The c200 antigen was used as a comparison it is presumed to be non-conformational due to the presence of reducing agent (DTT) and detergent (SDS) in its formulation.

The immunoreactivity was tested against two early HCV seroconversion panels, PHV 904 and PHV 914 (commercially available human blood samples from Boston Biomedica, Inc., West Bridgewater, Mass.). The results are shown in Table 9. The data suggest that the denatured or linearized form of NS3/4a (as well as c200) does not detect early seroconversion panels as early as the NS3/4a conformational epitope.

TABLE 9

|  |  | NS3/4a vs. denatured NS3/4a | | | | | |
|---|---|---|---|---|---|---|---|
|  |  | *Spiked 2% SDS to stock NS3/4a | | | | | |
|  |  | NS3/4a | dNS3/4a* | c200 | NS3/4a | dNS3/4a* | c200 |
|  |  | OD | OD | OD | s/co | s/co | s/co |
| HCV | PHV 904-1 | 0.012 | 0.012 | 0.009 | 0.02 | 0.02 | 0.01 |
| Seroconversions | PHV 904-2 | 0.011 | 0.009 | 0.008 | 0.02 | 0.01 | 0.01 |
|  | PHV 904-3 | 1.124 | 0.071 | 0.045 | 1.80 | 0.11 | 0.07 |
|  | PHV 904-4 | 2.401 | 0.273 | 0.129 | 3.85 | 0.44 | 0.21 |
|  | PHV 904-5 | 3.022 | 0.793 | 0.347 | 4.85 | 1.28 | 0.57 |
|  | PHV 904-6 | 2.711 | 1.472 | 0.774 | 4.35 | 2.37 | 1.28 |
|  | PHV 904-7 | 3.294 | 1.860 | 0.943 | 5.28 | 3.00 | 1.55 |
|  | PHV 914-1 | 0.006 | 0.004 | 0.001 | 0.01 | 0.01 | 0.00 |
|  | PHV 914-2 | 0.005 | 0.004 | 0.002 | 0.01 | 0.01 | 0.00 |
|  | PHV 914-3 | 0.098 | 0.003 | 0.001 | 0.16 | 0.00 | 0.00 |
|  | PHV 914-4 | 1.118 | 0.006 | 0.004 | 1.79 | 0.01 | 0.01 |
|  | PHV 914-5 | 2.035 | 0.044 | 0.022 | 3.26 | 0.07 | 0.04 |
|  | PHV 914-6 | 2.092 | 0.074 | 0.025 | 3.35 | 0.12 | 0.04 |
|  | PHV 914-7 | 2.519 | 0.281 | 0.132 | 4.04 | 0.45 | 0.22 |
|  | PHV 914-8 | 2.746 | 0.907 | 0.500 | 4.40 | 1.46 | 0.82 |
|  | PHV 914-9 | 3.084 | 1.730 | 0.931 | 4.94 | 2.78 | 1.53 |
| HCV 3.0 | Neg.Cont. | 0.023 | 0.024 | 0.008 |  |  |  |
| Controls | Neg.Cont. | 0.027 | 0.024 | 0.007 |  |  |  |
|  | Neg.Cont. | 0.021 | 0.017 | 0.005 |  |  |  |
|  | average | 0.024 | 0.022 | 0.007 |  |  |  |
|  | cutoff | 0.624 | 0.622 | 0.607 |  |  |  |
|  | Pos. Cont. | 1.239 | 0.903 | 0.575 | 1.99 | 1.45 | 0.95 |
|  | Pos. Cont. | 1.445 | 0.916 | 0.614 | 2.32 | 1.47 | 1.01 |

Immunoreactivity of the conformational epitope was also tested using monoclonal antibodies to NS3/4a, made using standard procedures. These monoclonal antibodies were then tested in the ELISA format against NS3/4a and denatured NS3/4a and c200 antigen. The data show that anti-NS3/4a monoclonals react to the NS3/4a and denatured NS3/4a in a similar manner to the seroconversion panels shown in Table 10. This result also provides further evidence that the NS3/4a is conformational in nature as monoclonal antibodies can be made which are similar in reactivity to the early c33c seroconversion panels.

TABLE 10

| Monoclonal | Plate | NS3/4a OD | dNS3/4a OD | c200 OD |
|---|---|---|---|---|
| 4B9/E3 | 1:100 | 1.820 | 0.616 | 0.369 |
|  | 1:1000 | 1.397 | 0.380 | 0.246 |
|  | 1:10000 | 0.864 | 0.173 | 0.070 |
|  | 1:20000 | 0.607 | 0.116 | 0.085 |
| 5B7/D7 | 1:100 | 2.885 | 0.898 | 0.436 |
|  | 1:1000 | 2.866 | 0.541 | 0.267 |
|  | 1:10000 | 1.672 | 0.215 | 0.086 |
|  | 1:20000 | 1.053 | 0.124 | 0.059 |
| 1A8/H2 | 1:100 | 1.020 | 0.169 | 0.080 |
|  | 1:1000 | 0.921 | 0.101 | 0.043 |
|  | 1:10000 | 0.653 | 0.037 | 0.013 |
|  | 1:20000 | 0.337 | 0.027 | 0.011 |

Accordingly, novel HCV detection assays have been disclosed. From the foregoing, it will be appreciated that, although specific embodiments of the invention have been described herein for purposes of illustration, various modifications may be made without deviating from the spirit and scope of the disclosure herein.

What is claimed is:

1. An immunoassay solid support comprising at least one hepatitis C virus (HCV) anti-core antibody and at least one isolated HCV NS3/4a epitope bound thereto, wherein said NS3/4a epitope comprises the amino acid sequence depicted in FIGS. 4A–4D, or an amino acid sequence with at least 80% sequence identity thereto which has protease activity.

2. The immunoassay solid support of claim 1, comprising at least two HCV anti-core antibodies bound thereto.

3. The immunoassay solid support of claim 1, wherein said at least one anti-core antibody is directed against an N-terminal region of the HCV core antigen.

4. The immunoassay solid support of claim 3, wherein said at least one anti-core antibody is directed against amino acids 10–53 of HCV, numbered relative to the HCV1 polyprotein sequence.

5. The immunoassay solid support of claim 1, wherein said at least one anti-core antibody is a monoclonal antibody.

6. The immunoassay solid support of claim 1, wherein said NS3/4a epitope is a conformational epitope and comprises the amino acid sequence depicted in FIGS. 4A–4D.

7. The immunoassay solid support of claim 1, further comprising a multiple epitope fusion antigen bound thereto.

8. The immunoassay solid support of claim 7, wherein said multiple epitope fusion antigen comprises the amino acid sequence depicted in FIGS. 7A–7F.

9. A method of detecting hepatitis C virus (HCV) infection in a biological sample, said method comprising:

(a) providing an immunoassay solid support according to claim 1;

(b) combining a biological sample with said solid support under conditions which allow HCV antigens and antibodies, when present in the biological sample, to bind to said at least one anti-core antibody and said NS3/4a epitope, respectively;

(c) adding to the solid support from step (b) under complex forming conditions (i) a first detectably labeled antibody, wherein said first detectably labeled antibody is a detectably labeled HCV anti-core antibody, wherein said labeled anti-core antibody is directed against a different HCV core epitope than the at least one anti-core antibody bound to the solid support; (ii) an antigen that reacts with an HCV antibody from the biological sample reactive with said NS3/4a epitope; and (iii) a second detectably labeled antibody, wherein said second detectably labeled antibody is reactive with the antigen of (ii);

(d) detecting complexes formed between the antibodies and antigens, if any, as an indication of HCV infection in the biological sample.

10. The method of claim 9, wherein said at least one anti-core antibody is directed against an N-terminal region of the HCV core antigen and said detectably labeled HCV anti-core antibody is directed against a C-terminal region of the HCV core antigen.

11. The method of claim 10, wherein said at least one anti-core antibody is directed against amino acids 10–53 of HCV, numbered relative to the HCV1 polyprotein sequence and said detectably labeled HCV anti-core antibody is directed against amino acids 120–130 of HCV, numbered relative to the HCV1 polyprotein sequence.

12. The method of claim 9, wherein said antigen that reacts with an HCV antibody from the biological sample comprises an epitope from the c33c region of the HCV polyprotein.

13. The method of claim 12, wherein the c33c epitope is fused with a human superoxide dismutase (hSOD) amino acid sequence and the second detectably labeled antibody is reactive with said hSOD amino acid sequence.

14. The method of claim 9, wherein said NS3/4a epitope is a conformational epitope and comprises the amino acid sequence depicted in FIGS. 4A–4D.

15. A method of detecting hepatitis C virus (HCV) infection in a biological sample, said method comprising:
(a) providing an immunoassay solid support according to claim 2;
(b) combining a biological sample with said solid support under conditions which allow HCV antigens and antibodies, when present in the biological sample, to bind to the said at least two anti-core antibodies and said NS3/4a epitope, respectively;
(c) adding to the solid support from step (b) under complex forming conditions (i) a first detectably labeled antibody, wherein said first detectably labeled antibody is a detectably labeled HCV anti-core antibody, wherein said labeled anti-core antibody is directed against a different HCV core epitope than the at least two anti-core antibodies bound to the solid support; (ii) an epitope from the c33c region of the HCV polyprotein fused to an hSOD amino acid sequence; and (iii) a second detectably labeled antibody, wherein said second detectably labeled antibody is reactive with said hSOD amino acid sequence;
(d) detecting complexes formed between the antibodies and antigens, if any, as an indication of HCV infection in the biological sample.

16. The method of claim 15, wherein said NS3/4a epitope is a conformational epitope and comprises the amino acid sequence depicted in FIGS. 4A–4D.

17. A method of detecting hepatitis C virus (HCV) infection in a biological sample, said method comprising:
(a) providing an immunoassay solid support according to claim 7;
(b) combining a biological sample with said solid support under conditions which allow HCV antigens and antibodies, when present in the biological sample, to bind to said at least one anti-core antibody, said NS3/4a epitope, and said multiple epitope fusion antigen;
(c) adding to the solid support from step (b) under complex forming conditions (i) a first detectably labeled antibody, wherein said first detectably labeled antibody is a detectably labeled HCV anti-core antibody, wherein said labeled anti-core antibody is directed against a different HCV core epitope than the at least one anti-core antibody bound to the solid support; (ii) first and second antigens that react with an HCV antibody from the biological sample reactive with said NS3/4a epitope and said multiple epitope fusion antigen, respectively; and (iii) a second detectably labeled antibody, wherein said second detectably labeled antibody is reactive with the antigens of (ii);
(d) detecting complexes formed between the antibodies and antigens, if any, as an indication of HCV infection in the biological sample.

18. The method of claim 17, wherein said at least one anti-core antibody is directed against an N-terminal region of the HCV core antigen and said first detectably labeled HCV anti-core antibody is directed against a C-terminal region of the HCV core antigen.

19. The method of claim 18, wherein said at least one anti-core antibody is directed against amino acids 10–53 of HCV, numbered relative to the HCV1 polyprotein sequence and said detectably labeled HCV anti-core antibody is directed against amino acids 120–130 of HCV, numbered relative to the HCV1 polyprotein sequence.

20. The method of claim 17, wherein said first antigen that reacts with an HCV antibody from the biological sample comprises an epitope from the c33c region of the HCV polyprotein.

21. The method of claim 20, wherein the c33c epitope is fused with a human superoxide dismutase (hSOD) amino acid sequence and the second detectably labeled antibody is reactive with said hSOD amino acid sequence.

22. The method of claim 17, wherein said second antigen that reacts with an HCV antibody from the biological sample comprises an epitope from the c22 region of the HCV polyprotein.

23. The method of claim 22, wherein the epitope from the c22 region comprises amino acids $Lys_{10}$ to $Ser_{99}$ of the HCV polyprotein, with a deletion of Arg47 and a substitution of Leu for Trp at position 44, numbered relative to the HCV1 polyprotein sequence, wherein said epitope is fused with a human superoxide dismutase (hSOD) amino acid sequence and the second detectably labeled antibody is reactive with said hSOD amino acid sequence.

24. The method of claim 17, wherein said multiple epitope fusion antigen comprises the amino acid sequence depicted in FIGS. 7A–7F.

25. An immunodiagnostic test kit comprising the immunoassay solid support of claim 1, and instructions for conducting the immunodiagnostic test.

26. An immunoassay solid support comprising two hepatitis C virus (HCV) anti-core monoclonal antibodies and an HCV NS3/4a conformational epitope comprising the amino acid sequence depicted in FIGS. 4A–4D, bound thereto.

27. The immunoassay solid support of claim 26, wherein said two anti-core antibodies are directed against an N-terminal region of the HCV core antigen.

28. The immunoassay solid support of claim 27, wherein said two anti-core antibodies are directed against amino acids 10–53 of HCV, numbered relative to the HCV1 polyprotein sequence.

29. A method of detecting hepatitis C virus (HCV) infection in a biological sample, said method comprising:
(a) providing an immunoassay solid support according to claim 26;
(b) combining a biological sample with said solid support under conditions which allow HCV antigens and antibodies, when present in the biological sample, to bind to the said at least two anti-core antibodies and said NS3/4a conformational epitope, respectively;
(c) adding to the solid support from step (b) under complex forming conditions (i) a first detectably labeled antibody, wherein said first detectably labeled antibody is a detectably labeled HCV anti-core antibody, wherein said labeled anti-core antibody is directed against a different HCV core epitope than the at least two anti-core antibodies bound to the solid support; (ii) an epitope from the c33c region of the HCV polyprotein fused to an hSOD amino acid sequence; and (iii) a second detectably labeled antibody, wherein said second detectably labeled antibody is reactive with said hSOD amino acid sequence;
(d) detecting complexes formed between the antibodies and antigens, if any, as an indication of HCV infection in the biological sample.

30. The method of claim 29, wherein said at least two anti-core antibodies are directed against an N-terminal region of the HCV core antigen and said detectably labeled HCV anti-core antibody is directed against a C-terminal region of the HCV core antigen.

31. The method of claim 30, wherein said at least two anti-core antibodies are directed against amino acids 10–53 of HCV, numbered relative to the HCV1 polyprotein sequence and said detectably labeled HCV anti-core antibody is directed against amino acids 120–130 of HCV, numbered relative to the HCV1 polyprotein sequence.

32. An immunodiagnostic test kit comprising the immunoassay solid support of claim 26, and instructions for conducting the immunodiagnostic test.

33. An immunoassay solid support comprising two hepatitis C virus (HCV) anti-core monoclonal antibodies, an HCV NS3/4a conformational epitope comprising the amino acid sequence depicted in FIGS. 4A–4D, and a multiple epitope fusion antigen comprising the amino acid sequence depicted in FIGS. 7A–7F, bound thereto.

34. A method of detecting hepatitis C virus (HCV) infection in a biological sample, said method comprising:
(a) providing an immunoassay solid support according to claim 33;
(b) combining a biological sample with said solid support under conditions which allow HCV antigens and antibodies, when present in the biological sample, to bind to the said at least two anti-core antibodies, said NS3/4a conformational epitope, and said multiple epitope fusion antigen, respectively;
(c) adding to the solid support from step (b) under complex forming conditions (i) a first detectably labeled antibody, wherein said first detectably labeled antibody is a detectably labeled HCV anti-core antibody, wherein said labeled anti-core antibody is directed against a different HCV core epitope than the at least two anti-core antibodies bound to the solid support; (ii) an epitope from the c33c region of the HCV polyprotein fused to an hSOD amino acid sequence and an epitope from the c22 region of the HCV polyprotein fused to an hSOD amino acid sequence; and (iii) a second detectably labeled antibody, wherein said second detectably labeled antibody is reactive with said hSOD amino acid sequences;
(d) detecting complexes formed between the antibodies and antigens, if any, as an indication of HCV infection in the biological sample.

35. The method of claim 34, wherein said at least two anti-core antibodies are directed against an N-terminal region of the HCV core antigen and said detectably labeled HCV anti-core antibody is directed against a C-terminal region of the HCV core antigen.

36. The method of claim 35, wherein said at least two anti-core antibodies are directed against amino acids 10–53 of HCV, numbered relative to the HCV1 polyprotein sequence and said detectably labeled HCV anti-core antibody is directed against amino acids 120–130 of HCV, numbered relative to the HCV1 polyprotein sequence.

37. The method of claim 36, wherein the epitope from the c22 region comprises amino acids $Lys_{10}$ to $Ser_{99}$ of the HCV polyprotein, with a deletion of Arg47 and a substitution of Leu for Trp at position 44, numbered relative to the HCV1 polyprotein sequence.

38. An immunodiagnostic test kit comprising the immunoassay solid support of claim 33, and instructions for conducting the immunodiagnostic test.

39. A method of producing an immunoassay solid support, comprising:
(a) providing a solid support; and
(b) binding at least one hepatitis C virus (HCV) anti-core antibody and at least one isolated HCV NS3/4a conformational epitope thereto, wherein said NS3/4a epitope comprises the amino acid sequence depicted in FIGS. 4A–4D, or an amino acid sequence with at least 80% sequence identity thereto which has protease activity.

40. A method of producing an immunoassay solid support, comprising:
(a) providing a solid support; and
(b) binding two hepatitis C virus (HCV) anti-core antibodies and an isolated HCV NS3/4a conformational epitope thereto, wherein said NS3/4a epitope comprises the amino acid sequence depicted in FIGS. 4A–4D, or an amino acid sequence with at least 80% sequence identity thereto which has protease activity.

41. The method of claim 39, further comprising binding at least one multiple epitope fusion antigen to the solid support.

42. The method of claim 40, further comprising binding at least one multiple epitope fusion antigen to the solid support.

43. A method of producing an immunoassay solid support, comprising:
(a) providing a solid support; and
(b) binding two hepatitis C virus (HCV) anti-core antibodies, an isolated HCV NS3/4a conformational epitope, and a multiple epitope fusion antigen, thereto, wherein said NS3/4a epitope comprises the amino acid sequence depicted in FIGS. 4A–4D, or an amino acid sequence with at least 80% sequence identity thereto which has protease activity.

* * * * *